(12) United States Patent
Sochor

(10) Patent No.: US 8,162,684 B1
(45) Date of Patent: Apr. 24, 2012

(54) IMPLANTABLE CONNECTOR WITH CONTACT-CONTAINING FEEDTHROUGH PINS

(76) Inventor: Jerzy Roman Sochor, Sunnyvale, CA (US)

(*) Notice: Subject to any disclaimer, the term of this patent is extended or adjusted under 35 U.S.C. 154(b) by 0 days.

(21) Appl. No.: 12/882,072

(22) Filed: Sep. 14, 2010

Related U.S. Application Data

(63) Continuation-in-part of application No. 12/187,392, filed on Aug. 7, 2008, now Pat. No. 7,794,256.

(51) Int. Cl.
*H01R 13/28* (2006.01)

(52) U.S. Cl. .................... 439/289; 439/909
(58) Field of Classification Search .......... 439/73, 439/270, 289, 521, 668, 669, 909
See application file for complete search history.

(56) References Cited

U.S. PATENT DOCUMENTS

| 5,388,998 | A  | * | 2/1995  | Grange et al. | 439/66  |
|-----------|----|---|---------|---------------|---------|
| 6,321,126 | B1 | * | 11/2001 | Kuzma         | 607/137 |
| 6,662,035 | B2 | * | 12/2003 | Sochor        | 600/378 |
| 2003/0176113 | A1 | * | 9/2003 | Sasaki        | 439/700 |

* cited by examiner

*Primary Examiner* — Tulsidas C Patel
*Assistant Examiner* — Travis Chambers

(57) ABSTRACT

An implantable connector electrically connects multi-conductor leads to an implantable medical device such as a neurostimulator. The connector is assembled directly into a hermetic feedthrough of the device and utilizes the feedthrough housing as a sustaining structure for connector pressurization. The feedthrough pins are adapted to directly connect, confine, protect, and precisely position respective resilient compressible contacts. The compressible contacts can be coil springs, metal-particle-filled elastomer buttons, and fuzz buttons, and can be used with rigid tips where a contact preload and/or an enhanced contact tip robustness is desired. In one method of connector assembly an iso-diametric lead proximal terminal is first inserted into a seal without significant interference, and the resulting lead-seal assembly is subsequently installed in a clamping cover. Connector pressurization means include space-efficient latching clips and cam actuated clamping covers which support contact forces and the seal compression by engaging undercuts on the feedthrough housing side walls.

31 Claims, 24 Drawing Sheets

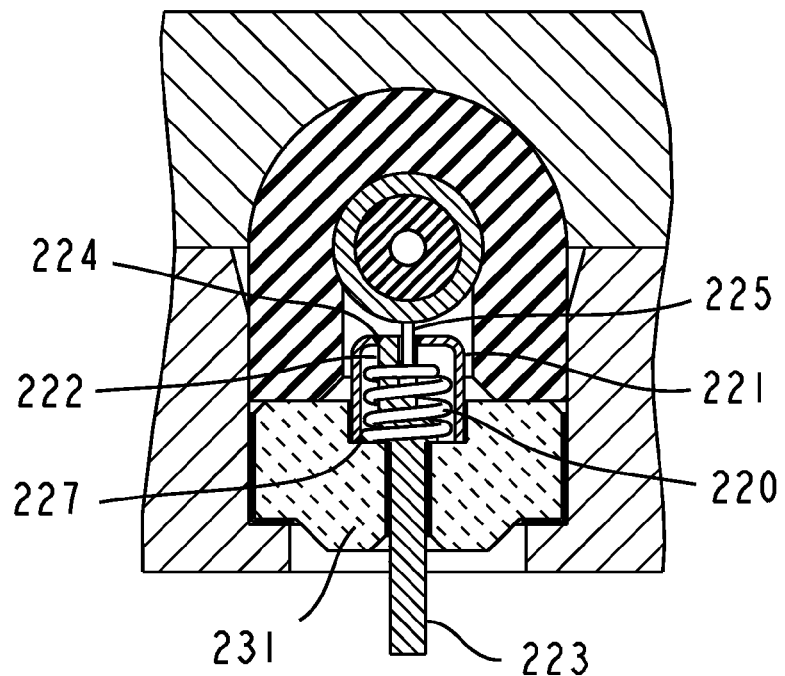
Fig. 27
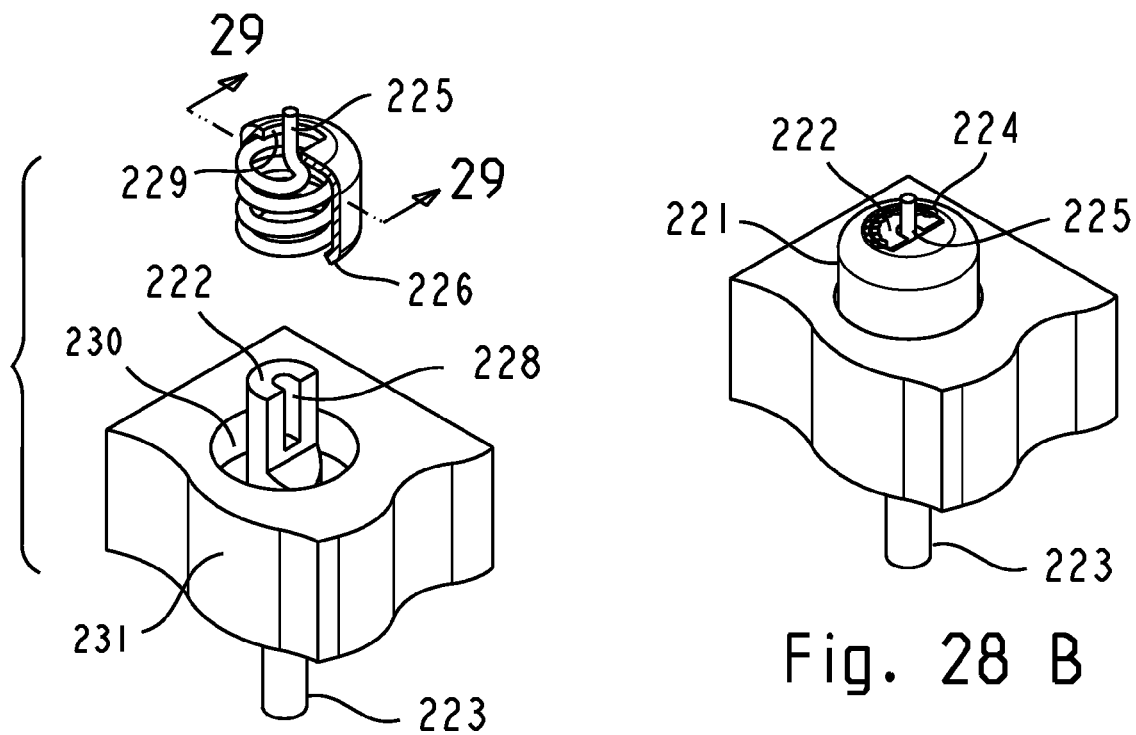
Fig. 28 A
Fig. 28 B

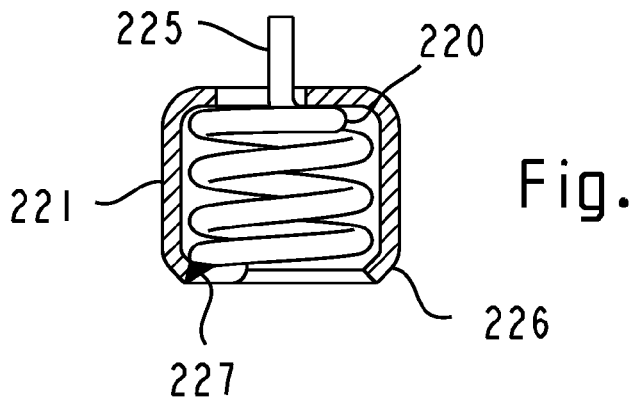
Fig. 29
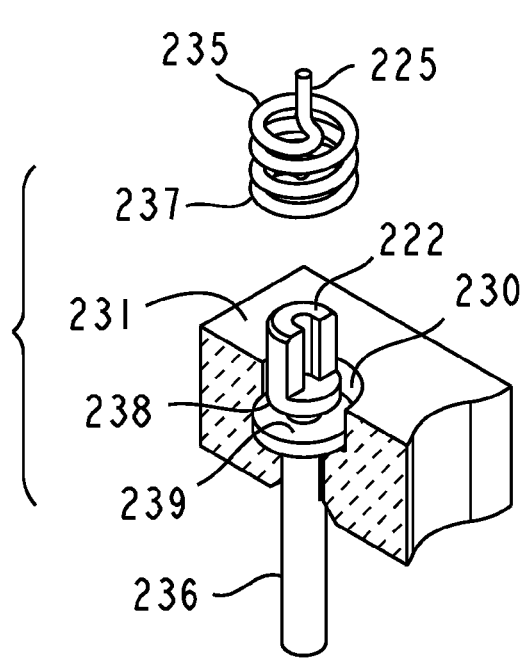
Fig. 30 A
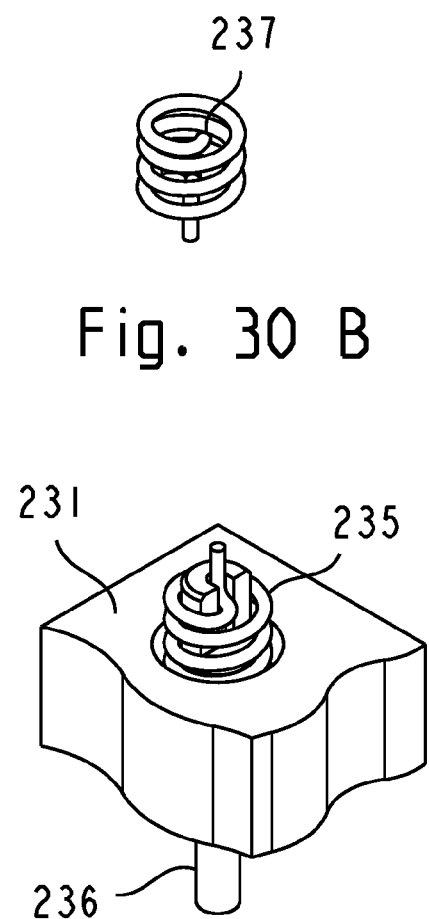
Fig. 30 B
Fig. 30 C

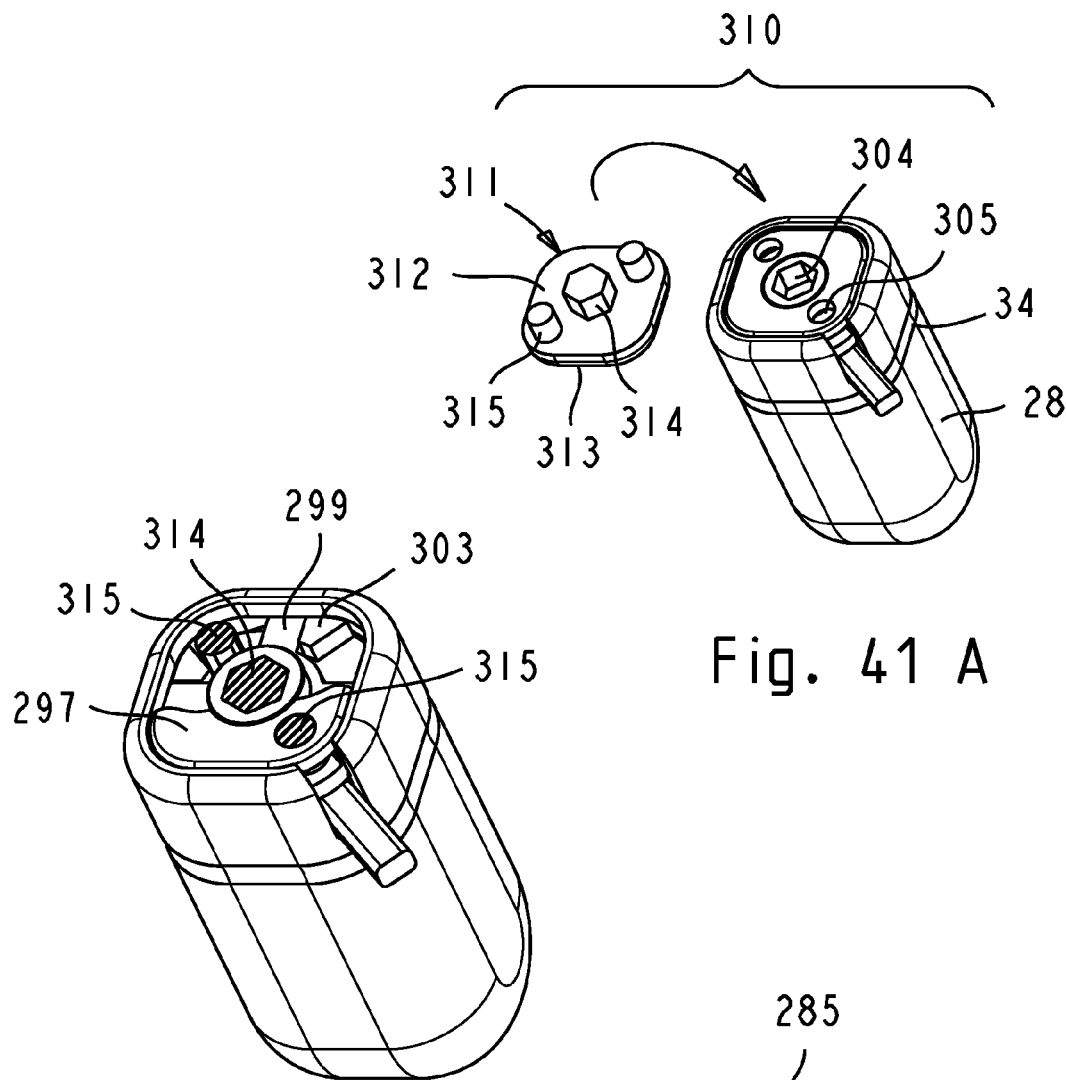
Fig. 41 A
Fig. 41 B
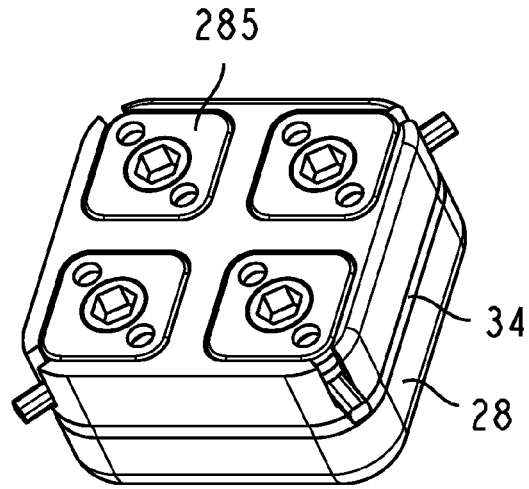
Fig. 42

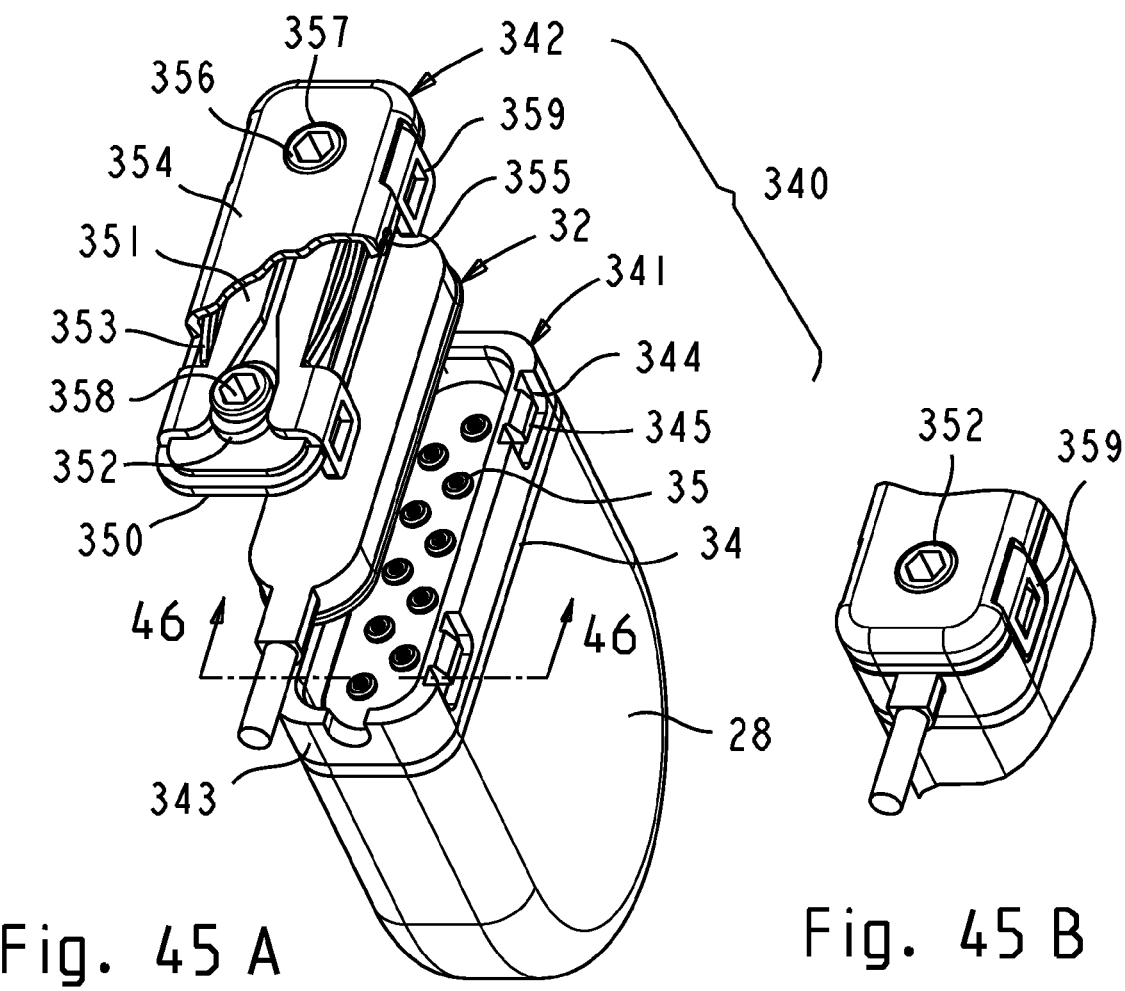
Fig. 45 A
Fig. 45 B
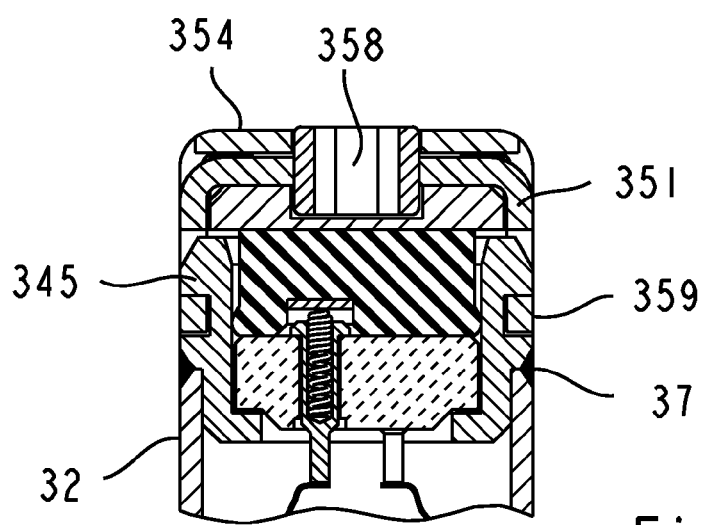
Fig. 46

IMPLANTABLE CONNECTOR WITH CONTACT-CONTAINING FEEDTHROUGH PINS

CROSS-REFERENCE TO RELATED APPLICATIONS

This is a continuation-in-part of application Ser. No. 12/187,392 filed 2008 Aug. 7, now U.S. Pat. No. 7,794,256 issued 2010 Sep. 14.

FEDERALLY SPONSORED RESEARCH

Not Applicable

SEQUENCE LISTING OR PROGRAM

Not Applicable

BACKGROUND

1. Field

This relates to implantable medical devices having external electrical connections and electrical feedthroughs, specifically to miniature implantable connectors for interconnection of implantable devices and associated lead wires.

2. Prior Art

In a typical implantable electronic device, such as a cochlear implant, heart pacemaker, or a brain-stimulating device, the device contains electronic circuitry (electronics) that resides in a hermetic housing or case. The device is attached to at least one electrical lead ("lead") that has sensing and/or stimulating electrodes on its end distal from the device. The electrodes are implanted in the tissue targeted for therapy (cochlea, heart muscle, particular area of brain, etc.). Other leads may connect the device to additional implantable system components, such as drug delivery devices, implantable inductive coils (for energy delivery to the device and/or data communication with the device), or power sources, which may have to reside in a more accessible body area for easier charging and/or replacement.

It is preferable that the implantable leads and devices be detachable so that either a device or leads can be implanted or explanted independently. This functionality is provided by a connector on the device's case, which disengageably connects the proximal (near-device) lead terminals to the device's electronics. The connector's contacts must connect with the device's electronics across a hermetic feedthrough so that the hermeticity of the device's case is not compromised, i.e., the electronics remains sealed from the body fluids and moisture. It is further desirable that the connector has a small size, can provide a rapid connection and disconnection without special tools, and allows multiple connect and disconnect cycles without loss of function.

In many existing devices the connector is implemented in a molded header (insulating housing), formed from a hard medical grade polymer on the edge of the device's case, and the connector's receptacle contacts are connected to the feedthrough pins by discrete wiring, which is subsequently overmolded (covered and sealed by insulating material). The wiring must interconnect two dissimilar and spatially separated contact patterns and can be quite intricate. The assembly and the associated molding and testing can be labor intensive, as discussed in U.S. Pat. No. 7,274,963 (2007) to Spadgenske.

The header connectors for iso-diametric (having constant diameter) leads typically have blind lead receiving lumens (i.e., the lumens are open at one end only) into which a lead is inserted with significant force (adequate to generate contact forces and compress the seals), so lead insertion force and contact registration can be an issue. The header connectors are therefore more suitable for larger-diameter, lower-contact-count leads, such as those used with cardiac rhythm management devices, which can tolerate significant insertion force and have more liberal contact registration tolerances.

U.S. Pat. No. 6,321,126 (2001) to Kuzma shows a header connector design for paddle-shaped lead terminals. This patent addresses the need for a high contact count, small-dimensioned connector, but this design is only applicable to leads with paddle-shaped lead terminals and cannot be adapted for iso-diametric lead terminals. In addition, the contact system appears to rely on an elastomeric backing of the lead terminal body for providing contact pressure. Since elastomeric materials are prone to time-dependent permanent deformation, contact pressure may relax with time, especially because such connections have a low compliance (independent of the elastic backing, the contacts have limited elastic deflection reserve). The low compliance is also problematic when repeated mating is required.

As the implantable medical devices and systems become more capable and number of the leads and the lead contact count and density increase, there is a need for small but robust connectors to make reliable connections to devices or components of the implantable system. The small size is especially important for devices such as neural and cochlear stimulators which are implanted in the cranium, both for medical reasons (a smaller cranial cavity needs to be created) and for aesthetic advantages. In such cases, it may be desirable to build the connector interface directly into the device's feedthrough housing cavity so that receptacle contacts are co-located with the feedthrough pins.

My U.S. Pat. No. 6,662,035 (2003) shows a feedthrough-based connector design intended for a device implantable beneath the scalp. This patent teaches how to implement reliable direct metal-to-metal connections between lead contacts and the corresponding feedthrough pins. The illustrative dimensions of the two-lead connector are a depth of approximately 6.5 mm, a length of approximately 15.0 mm, and a breadth of approximately 13.0 mm. These dimensions are still excessive for locating the connector on an edge of the device case or for use in size-critical subcutaneous applications, such as inside the cranium. Unfortunately, the size of the above feedthrough-based connector cannot be radically reduced due to the following factors:

(a) The device uses compressible contacts located entirely above the exterior (outwardly facing) surface of the feedthrough dielectric substrate, on which an interposer (seal) is seated. The entire compressible contact must be accommodated within the interposer thus adding to the total connector height.

(b) The compressible contacts use C-shaped springs having significant width and height that cannot be traded to reduce connector size. For a given spring-loop length, required for adequate contact force and deflection, a smaller contact height will lead to a greater contact width.

(c) The contact width controls the width of the interposer seal, and thus the connector's overall width.

(d) The spring contacts are free-standing and thus are susceptible to intra-operative handling damage if made too fragile. A smaller contact must be made from a thinner material (and thus would be more fragile) or it will be too stiff and have a low deflection capability. It is important that the contacts have adequate contact compliance or deflection range in order to accommodate assembly tolerances and to assure an adequate deflection reserve for repeated mating.

(e) A robust spring contact (necessary for the handling integrity) and a wide seal require substantial clamping hardware, including a relatively large screw. This larger screw causes the feedthrough area between the leads to be poorly utilized.

Another issue in miniature implantable connectors is protection of the implantable leads from handling damage, especially during intra-operative attachment of the leads to a connector. In order to protect the miniature implantable leads, the lead terminals may need to be pre-inserted into a lead-receiving connector component without significant insertion force. Subsequent handling can easily cause the leads to inadvertently retract prior to connector pressurization, causing a loss of contact registration.

SUMMARY

The present device, in one aspect, addresses the need for improved small implantable connectors built directly on a hermetic feedthrough of an implantable electronic device, such as a cochlear implant, a neurostimulator, a pacemaker, a pain-control device, and the like.

The connector in this aspect uses a contact system integrated with the feedthrough pin and a feedthrough housing as the sustaining structure for connector assembly and pressurization. The contact system consists of a feedthrough pin, a resilient compressible contact, and a means to position, secure, and protect the compressible contact.

Small connector size is realized by utilizing the feedthrough pin to directly interface, confine, protect, and precisely position the resilient contact element. The contact retention feature is provided by the feedthrough pin or by a separate component joined to the feedthrough pin.

A variety of compressible contacts can be used, including coil springs, fuzz buttons (a single length of a very fine wire formed into multiple small wavy loops), and metal-particle-filled elastomer buttons. These contact forms have been proven in many applications and can be economically produced in biocompatible versions. The compressible contacts may have a rigid tip or cup on the outer end to provide a more robust contact point and/or contact preload. The contact preload helps to assure a consistent contact force.

The connector can be adapted to connect implantable leads with a variety of lead proximal contact terminals, including, but not limited to, iso-diametric terminals with tubular or ring contacts and paddle-shaped terminals with planar contact pads.

In order to protect the miniature iso-diametric leads, a lead-proximal terminal is first inserted into a seal without encountering significant resistance. Once the lead is protected by the seal, the lead-seal assembly is subsequently lightly pressed into a cover or into a feedthrough cavity which retains and aligns the lead-seal assembly for the remaining steps of connector assembly and pressurization. Clamping options include space-efficient retention springs and clips.

DRAWINGS

FIG. 27 is a cross-sectional detail of a connector showing a coil spring contact contained in a tubular hat where the top of the hat is attached to the outer end of a slotted feedthrough pin.

FIGS. 28A-B are perspective views of the feedthrough contact assembly of FIG. 27.

FIG. 29 is a view of a coil spring contact assembled in a tubular hat, taken as indicated by the lines 29-29 of FIG. 28, showing a cross-sectional detail of the spring-to-hat weld.

FIGS. 30A-C show a coil spring contact assembly where the outer end of the coil spring is protected by a slotted outer end of the feedthrough pin.

Figure 31:
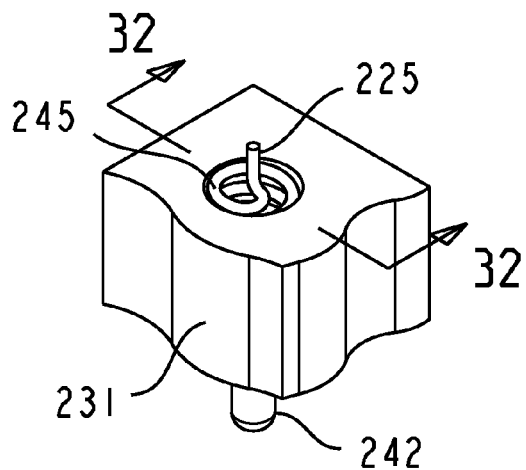

FIG. 31 shows a coil spring contact protectively confined within a counterbore on the outer side of the dielectric substrate.

Figure 32:
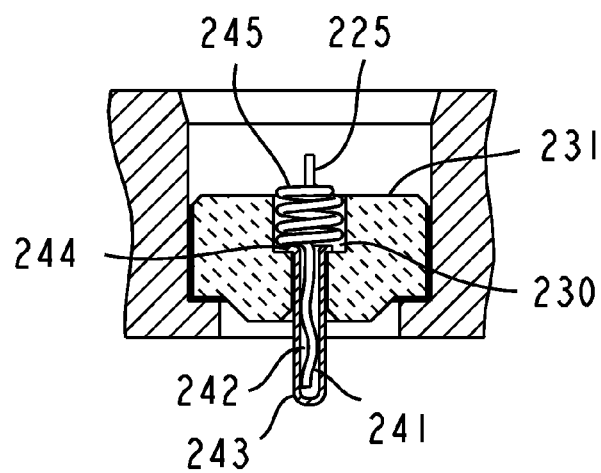

FIG. 32 is a cross-sectional view of FIG. 31, taken as indicated by the lines 32—32 of FIG. 31, showing the inner end extension of the coil spring retained by an interference fit in a tubular opening of the feedthrough pin.

Figure 33:
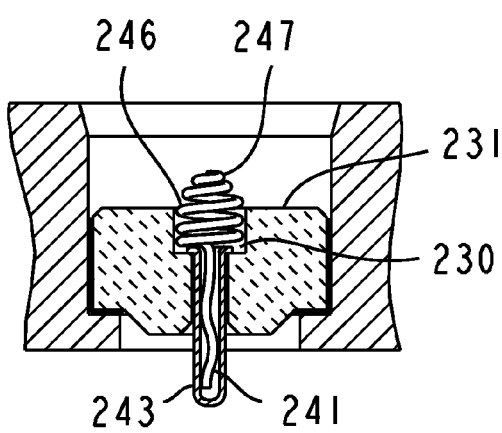

FIG. 33 is a variation of FIG. 32 showing a coil spring contact with a tapered outer end.

Figure 34:
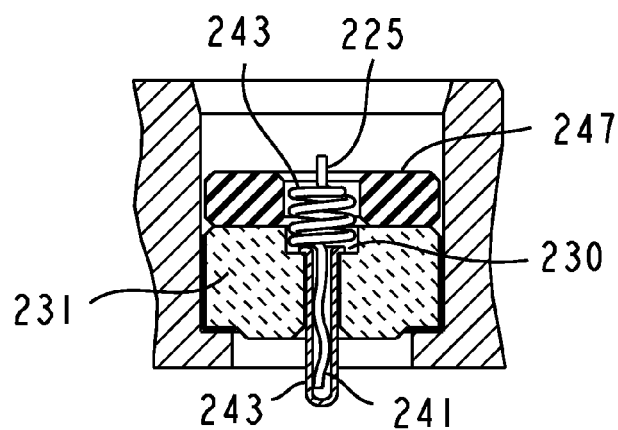

FIG. 34 is a variation of FIG. 32 showing a coil spring contact protectively confined in an opening of a discrete seal.

Figure 35:
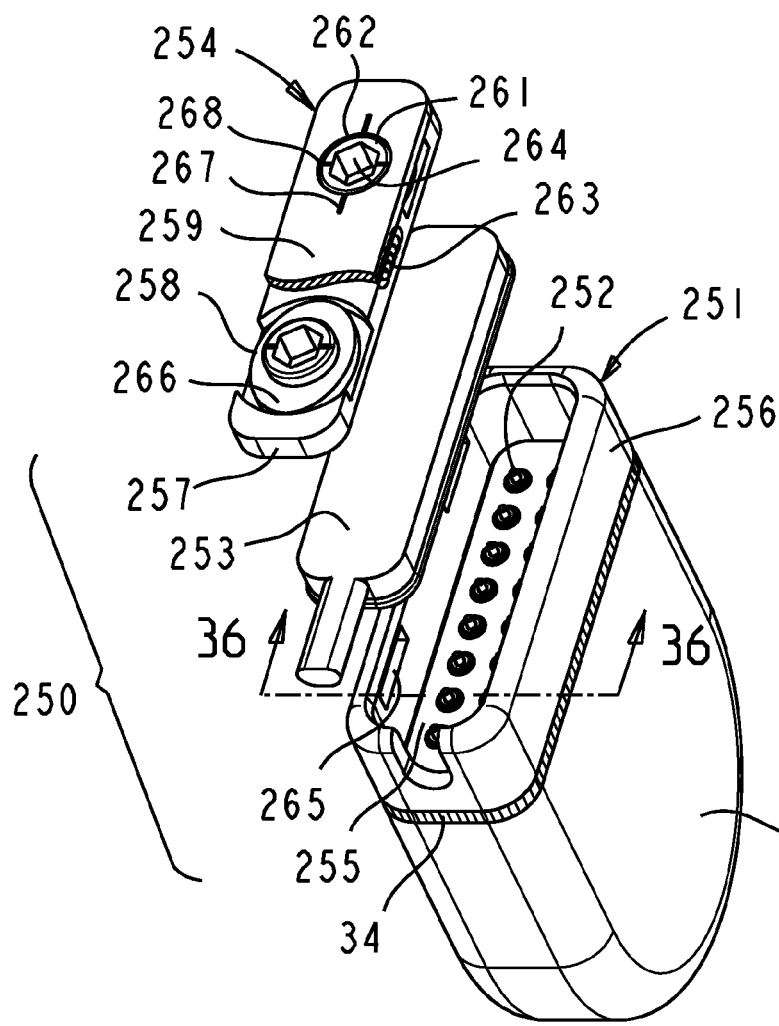

FIG. 35 is an exploded perspective view of an embodiment of the connector for leads with a paddle-shaped connector terminal, showing a device feedthrough with integrated compressible contacts, and a cam-driven clamping cover cooperating with undercuts on the inside walls of the feedthrough housing.

Figure 36:
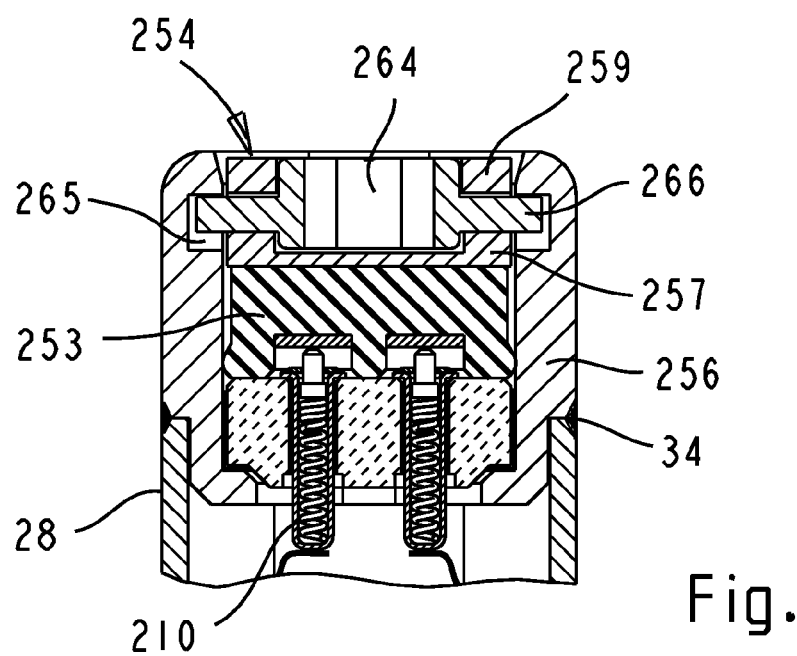

FIG. 36 is a partial cross-sectional view of the pressurized connector of FIG. 35, taken as indicated by the lines 36-36 of FIG. 35.

FIGS. 37A-C show a sequence of engaging the cam-driven clamping cover to the feedthrough housing.

Figure 38:
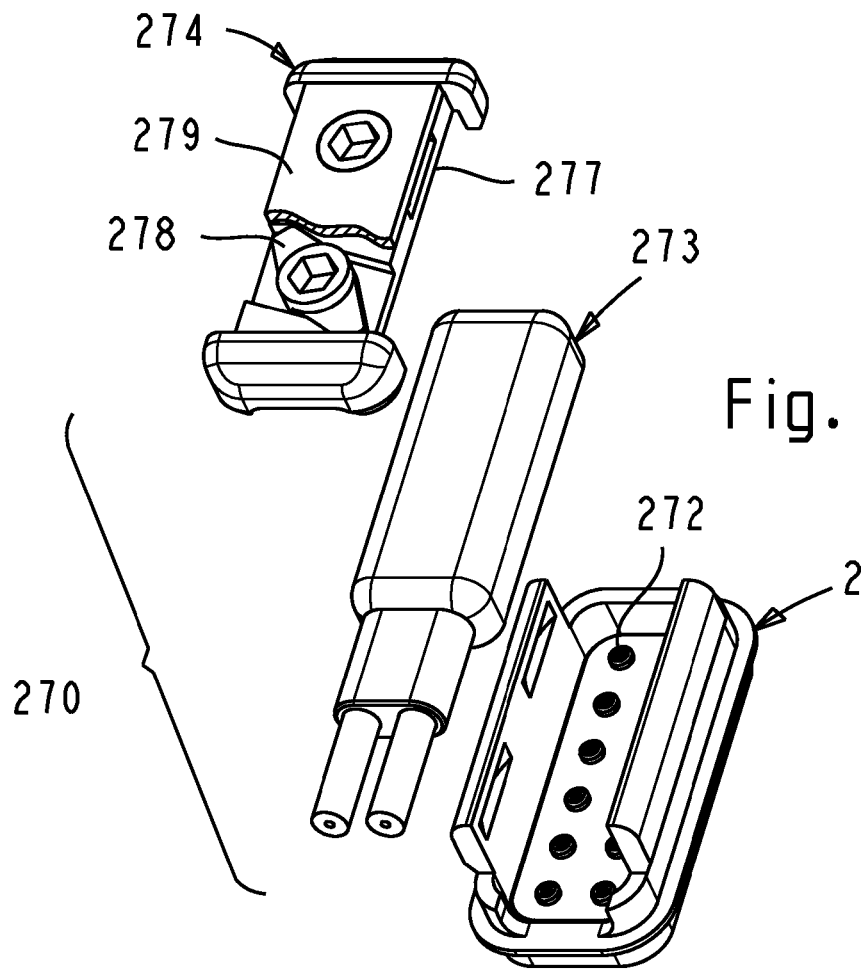
Figure 38:
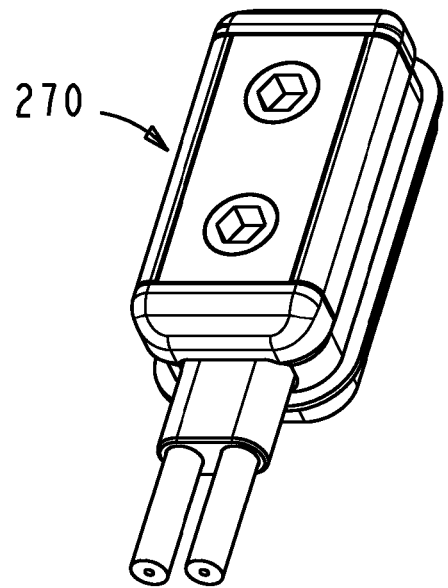

FIG. 38A is an exploded perspective view of an embodiment of the connector for iso-diametric leads, showing a device feedthrough with integrated compressible contacts, and a cam-driven clamping cover cooperating with undercuts on the inside walls of the feedthrough housing.

FIG. 38B is a perspective view of the connector of FIG. 38A in a pressurized state.

FIG. 39A is an exploded perspective view of an embodiment of a connector for two leads with paddle-shaped contact terminals, showing a device feedthrough with integrated compressible, contacts, discrete seals, and cam-driven clamping covers.

FIG. 39B is a perspective view of the connector of FIG. 39A in a pressurized state.

Figure 39:
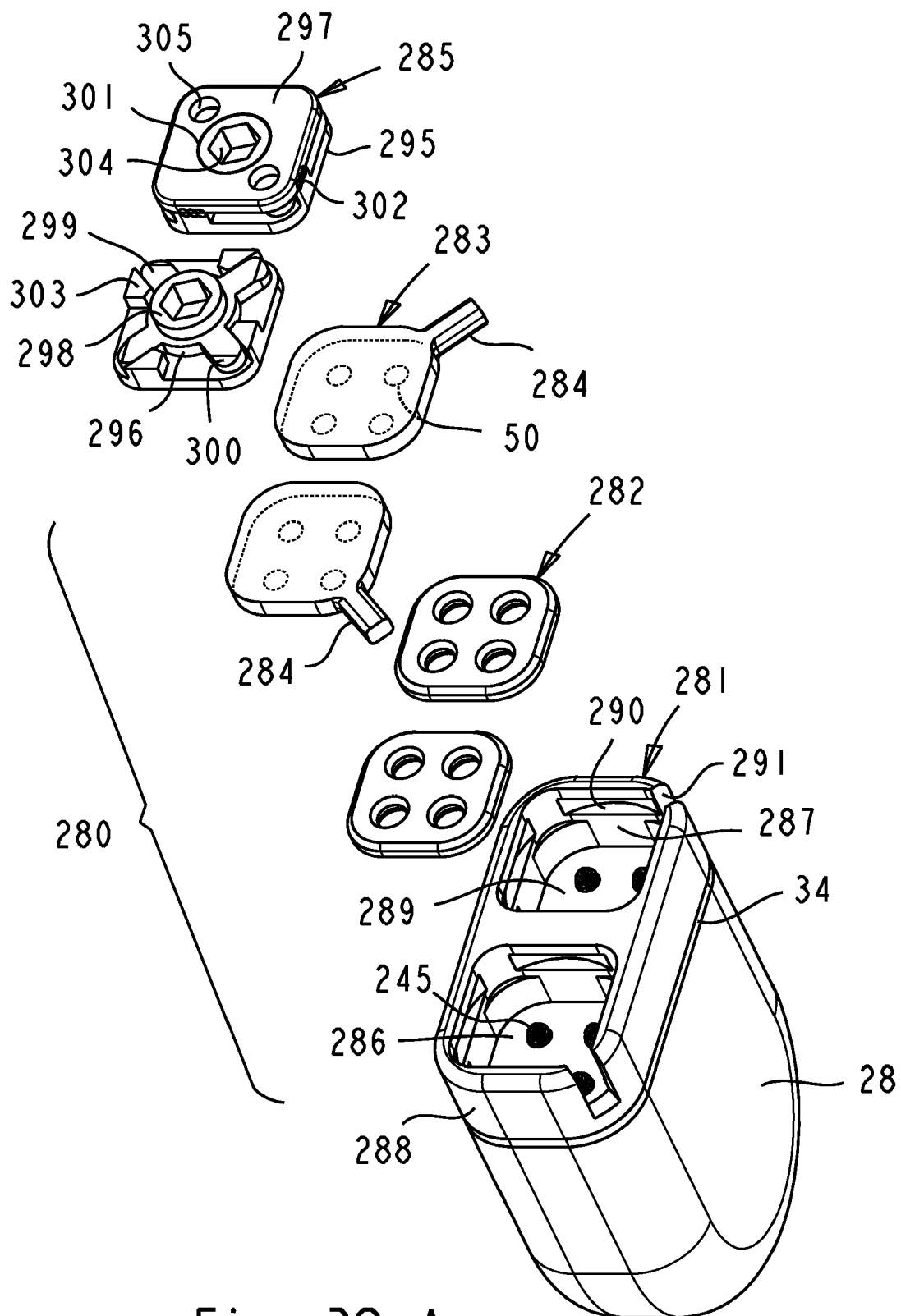
Figure 39:
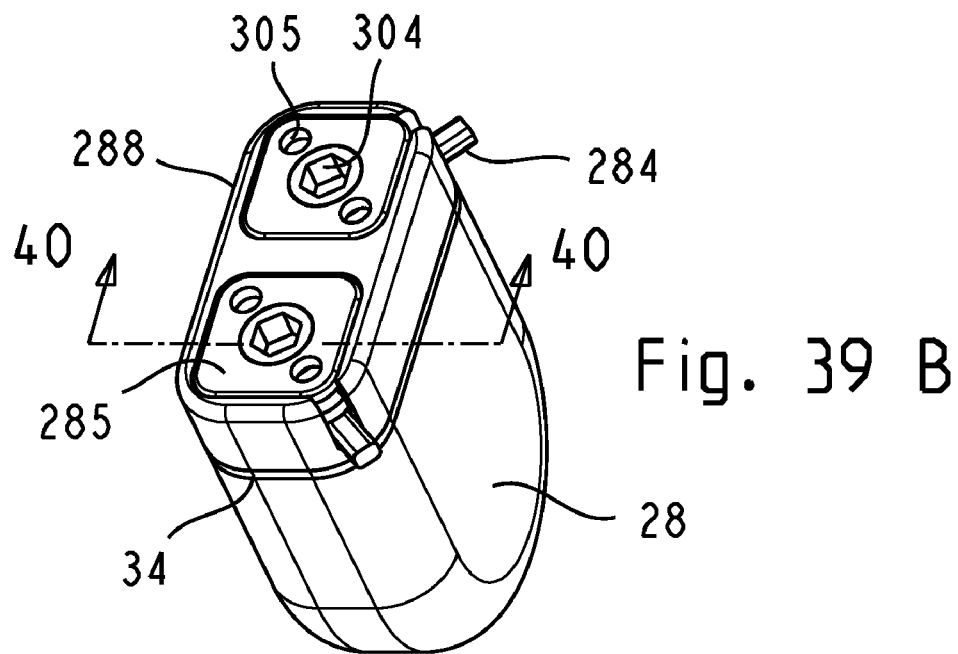
Figure 40:
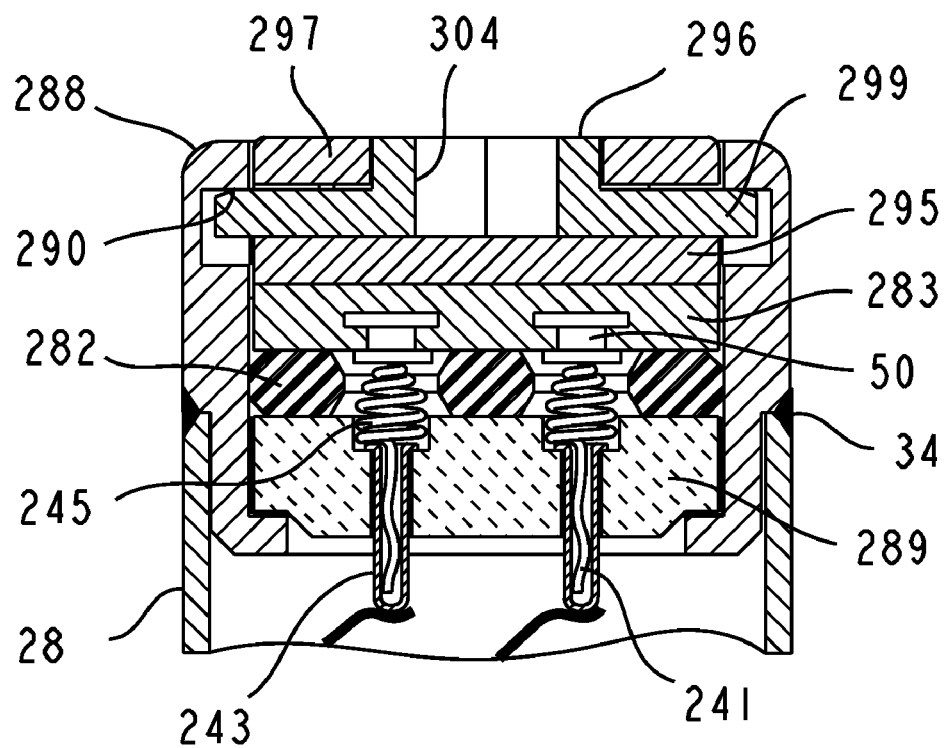

FIG. 40 is a partial cross-sectional view of the connector of FIG. 39B, taken as indicated by the lines 40-40 of FIG. 39B.

FIG. 41A-B are perspective views of a connector having a clamping cover with a means to securely maintain the clamping cover in the engaged condition.

FIG. 42 is a perspective view of a connector for four leads with paddle-shaped contact terminals where each lead terminal is accommodated in a separate feedthrough cavity and is clamped by a respective cam-driven clamping cover.

FIG. 43A is an exploded perspective view of an embodiment of a connector for four leads with paddle-shaped contact terminals, showing a device feedthrough with integrated compressible contacts, discrete seals, and a single cam-driven clamping cover.

FIG. 43B is a perspective view of the connector of FIG. 43A in a pressurized state.

Figure 43:
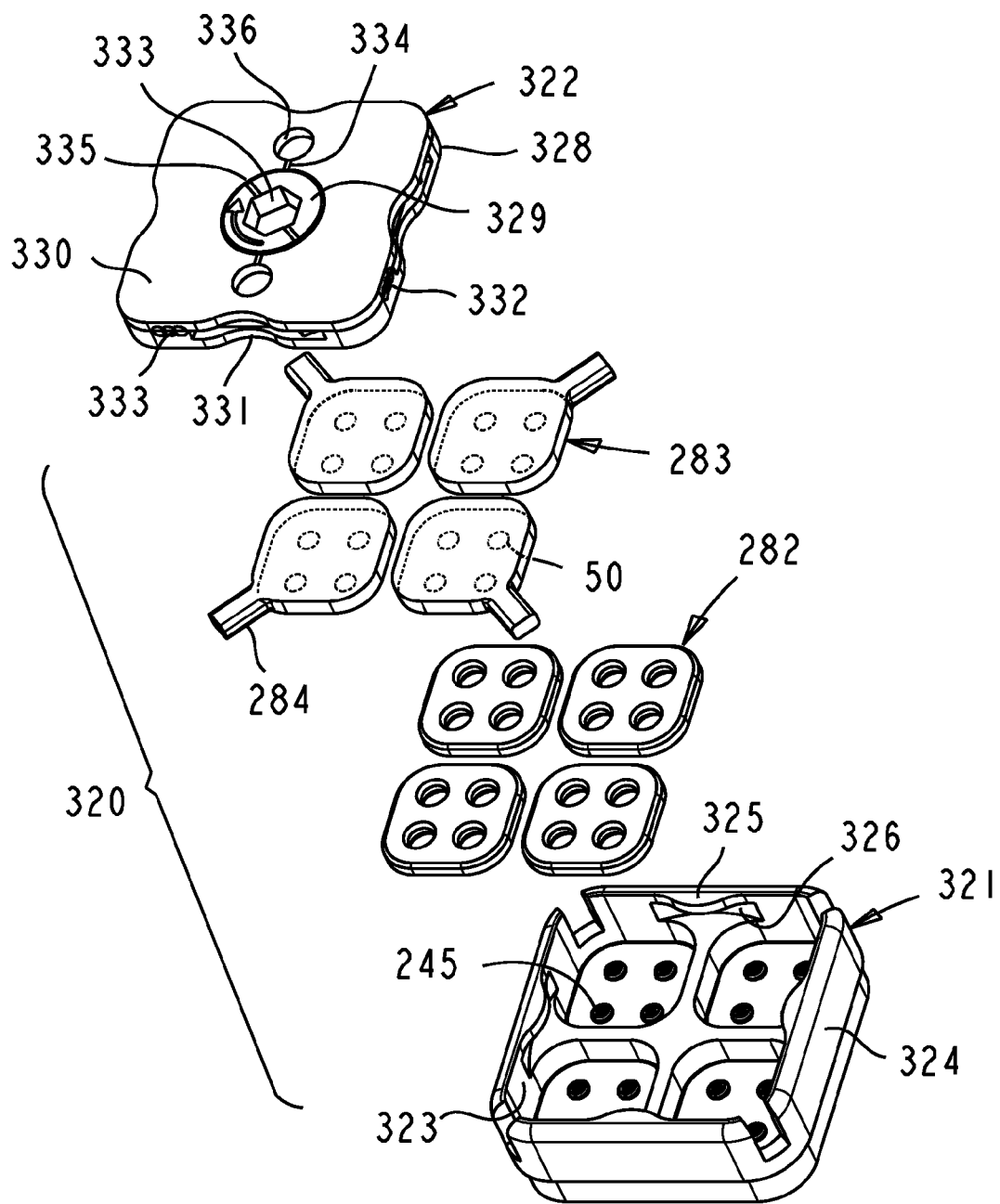
Figure 43:
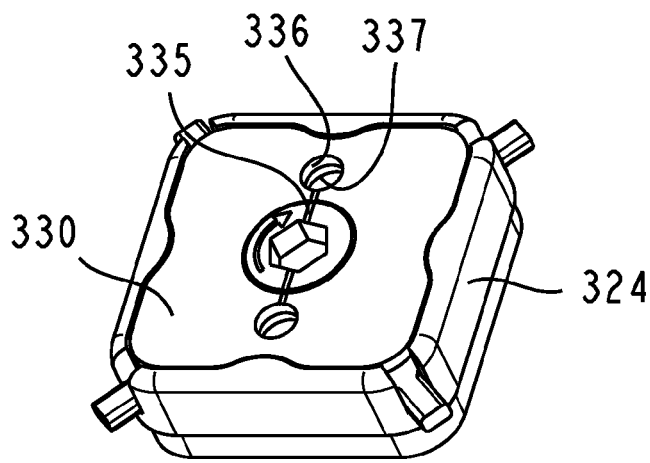
Figure 44:
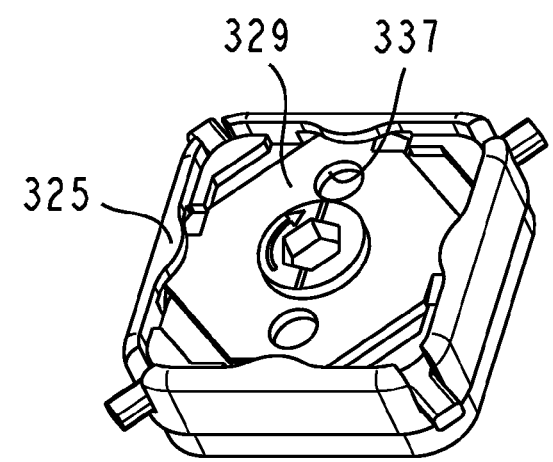
Figure 44:
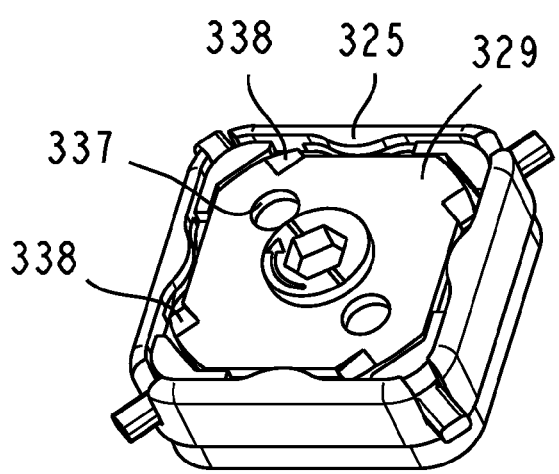

FIGS. 44A-B show the connector of FIG. 43B with the top cover plate removed to show the clamping cover cam in closed and open positions respectively.

Figure 1:
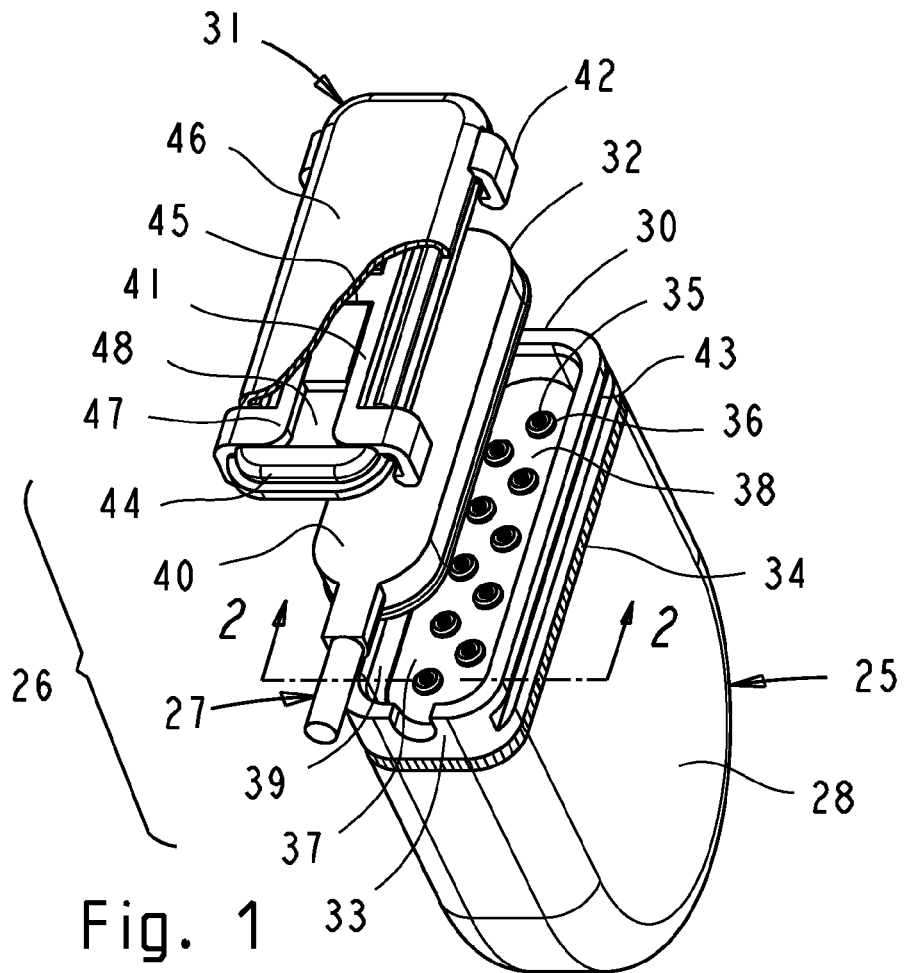
FIG. 1 is an exploded perspective view of an embodiment of the connector for a lead with a paddle-shaped contact terminal, showing a device feedthrough with integrated compressible contacts, and a clamping cover.

FIG. 45A is an exploded perspective view of a connector similar to that in FIG. 1, having a clamping cover with cam-actuated latches for engaging undercuts on the outside walls of the feedthrough housing.

FIG. 45B is a partial perspective view of the assembled connector of FIG. 45A.

FIG. 46 is a partial cross-sectional view of the pressurized connector of FIG. 45B, taken as indicated by the lines 46-46 of FIG. 45A.

REFERENCE NUMERALS 25 device
26 connector
27 lead
28 case, device
30 feedthrough assembly
31 clamping cover
32 lead terminal, paddle-shaped
33 feedthrough housing
34 weld line
35 compressible contact
36 feedthrough pin
37 feedthrough cavity
38 dielectric substrate
39 side wall, feedthrough cavity
40 lead terminal body
41 spring
42 latch
43 undercut, feedthrough housing
44 compression plate
45 mid-section, spring
46 cover, clamp
47 free end, spring
48 space
50 lead contact
54 feedthrough housing
55 welding flange
56 pressurization spring
59 feedthrough housing
60 feedthrough assembly
61 tubular section, feedthrough pin
62 outer end, compressible contact
63 inner end, compressible contact
64 rib, peripheral seal
65 latch
66 front end, retention spring
67 groove
68 back end, retention spring
70 connector
71 feedthrough assembly
72 compressible contact assembly
73 lead terminal 74 lead contact
75 seal
76 cover
77 clamping screw
78 seal lumen
79 channel
80 cover assembly
81 narrowing of channel
82 aperture, seal
83 alignment bosses
84 slotted hole
85 compressible contact
86 feedthrough pin
87 tubular section
88 dielectric substrate
89 top, compressible contact
90 rim, top of tubular section
91 exterior surface, substrate
95 connector
96 feedthrough assembly
97 compressible contact assembly
98 lead terminal
99 lead contact, tubular
100 seal
101 cover, clamping
102 retention clip
103 exterior cavity, feedthrough
104 dielectric substrate
105 inside wall, feedthrough housing
106 seal lumen
107 latch
108 undercut
109 relief cut, cover
110 mid-section, undercut
111 compressible contact
112 rigid contact insert
113 collar, feedthrough pin
114 insert, retaining
115 tip, contact insert
120 connector
121 feedthrough assembly
122 feedthrough housing
123 lead terminal
124 lead contact, tubular
125 seal, dual lead
126 cover, clamping
127 retention clip
128 exterior cavity, feedthrough
129 dielectric substrate
130 inside wall, feedthrough
131 seal lumen
132 latch
133 undercut
134 relief cut, cover
135 mid-section undercut
140 seal, Ω-profiled
141 cover, clamping
142 Ω-profiled channel
143 cover protrusion
147 spring sleeve
150 compressible contact
151 feedthrough pin
152 tubular section, feedthrough pin
155 compressible contact
156 plunger
157 hat, snap-on
158 dimple
159 feedthrough pin
160 contact top
161 compressible contact
162 hat
163 dimple
164 feedthrough pin
170 compressible contact, coil spring
171 hat
172 feedthrough pin
173 nail head
174 hole
175 end, spring
180 feedthrough pin
181 tubular section
182 compressible contact
183 bottom, dielectric substrate
184 crimp, feedthrough pin
190 compressible contact
191 contact tip insert
192 shank
193 shoulder
194 weld
201 feedthrough pin, tubular
202 contact, coil spring
203 tip, contact
204 tip, necked portion
205 outer end, crimped
206 form, circumferential
210 feedthrough pin, tubular
211 flange, feedthrough pin
212 counterbore, dielectric substrate
213 contact tip, rigid
214 insert
215 weld
220 contact, coil spring
221 hat
222 profiled head, feedthrough pin
223 feedthrough pin
224 weld
225 filar, centrally extending
226 bottom, hat
227 weld, spring-to-hat
228 slot, feedthrough pin
229 cutout, hat top
230 counterbore, dielectric substrate
231 dielectric substrate
235 contact, coil spring
236 feedthrough pin
237 inner end, spring
238 undercut, feedthrough pin
239 shoulder, feedthrough pin
241 tail, centrally extending
242 tubular opening, pin
243 feedthrough pin
244 flange, tubular pin
245 coil spring contact
246 coil spring, tapered end
247 outer end, tapered
250 connector
251 feedthrough assembly
252 contact
253 lead terminal, paddle-shaped
254 clamping cover
255 exterior cavity, feedthrough
256 feedthrough housing
257 bottom plate, clamping cover
258 cam 259 top plate, clamping cover
261 hub, cam
262 hole, top plate
263 weld joint
264 hex hole
265 undercut, inside walls
266 long side, cam
267 marking, cover
268 marking, cam
270 connector
271 feedthrough assembly
272 compressible contacts
273 lead-seal assembly
274 clamping cover
277 bottom plate
278 cam
279 top plate
280 connector
281 feedthrough assembly
282 seal, discrete
283 connector terminal, lead
284 lead
285 clamping cover
286 exterior cavity, feedthrough
287 inside wall, feedthrough
288 feedthrough housing
289 dielectric substrate
290 undercuts, inside walls
291 slot, lead exit
295 bottom plate
296 cam
297 top plate
298 hub, cam
299 arm, cam
300 taper, cam arm
301 central hole, top plate
302 weld
303 post, bottom plate
304 hex hole
305 utility hole
310 device
311 protective plug
312 inner side, plug
313 outer side, plug
314 hex protrusion, plug
315 round protrusion, plug
320 connector
321 feedthrough assembly
322 clamping cover
323 inside wall, feedthrough housing
324 feedthrough housing
325 mid-side protrusions
326 undercut, inside wall
328 clamping cover
329 cam
330 top plate
331 mid-side relief
332 weld joint
333 hex hole
334 alignment mark, cover
335 alignment mark, cam
336 utility hole, top plate
337 utility hole, cam
338 taper, cam
340 connector
341 feedthrough assembly
342 clamping cover
343 feedthrough housing
344 undercuts, U-shaped
345 detent, feedthrough housing
350 base plate
351 latching member
352 cam
353 bias spring
354 lid, clamping cover
355 weld, lid-to-base plate
356 hub, cam
357 hole, lid
358 hex hole, cam
359 latch, clamping cover

DETAILED DESCRIPTION

FIGS. 1-4—Embodiments for Leads with Flat Terminals

FIG. 1 is an exploded perspective view of an implantable device 25 with a connector 26 for detachably connecting an electrode lead 27 to the device's electronic circuitry contained in a hermetically sealed case 28.

Device 25 is designed to be implanted subcutaneously and/or in a body cavity, typically in a chest or in a cranium. The lead has multiple conductors (not shown) and extends from the device (proximal end) to the tissue targeted for sensing and/or stimulation (distal end), where the conductors connect to the lead's sensing and/or stimulating electrodes (not shown).

The connector's functional parts include a hermetic electrical feedthrough 30, a clamping cover 31, and a lead terminal 32. A separable mating interface is built directly into a hermetic feedthrough housing 33, which is attached to case 28 along a weld line 34. The connector mating interface has an array of compressible contacts 35 integrated with feedthrough pins 36 of feedthrough 30. (Only the top of pin 36 is shown in FIG. 1, but one is shown cross-sectioned in FIG. 2.) The mating ends or tips of compressible contacts protrude into a feedthrough exterior cavity 37 which is defined by the exterior side of a dielectric substrate 38 and inside walls 39 of housing 33.

Lead terminal 32 has a flat, paddle-shaped body 40 with an array of contact pads 50 (FIG. 2) which are connected to the respective conductors of lead 27, and are disposed in a pattern directly mapped to the corresponding array of feedthrough pins 36. The terminal body cooperates with feedthrough exterior cavity 37 to align the array of compressible contacts 35 with the corresponding array of contact pads 50, and to provide contact electrical isolation seals.

Clamping cover assembly 31 has a captive spring 41 which provides engagement latches 42 for disengageably locking the clamping cover against undercuts 43 on the outside walls of feedthrough housing 33. The spring can be attached to compression plate 44 at mid-section 45, e.g., by laser welding, and capped with an optional snap-on cover 46, preferably made out of bio-compatible polymer. The latches can be disengaged by spreading the springs outwardly at free ends 47, using a simple tool such as screwdriver in space 48 between the spring free ends. The spring can be stamped or machined from a biocompatible springy alloy, such as titanium alloy 6Al-4V. The compression plate can also be made from titanium or a titanium alloy. The optional cover can be molded from a biocompatible polymer or a medical grade elastomer if desirable. Alternatively, the top cover can be made out of a hard polymer or a metal and joined to the compression plate along its perimeter. The thus contained spring can be actuated through openings in the cover, e.g., using a built-in actuating cam between the spring's free ends (not shown).

Figure 2:
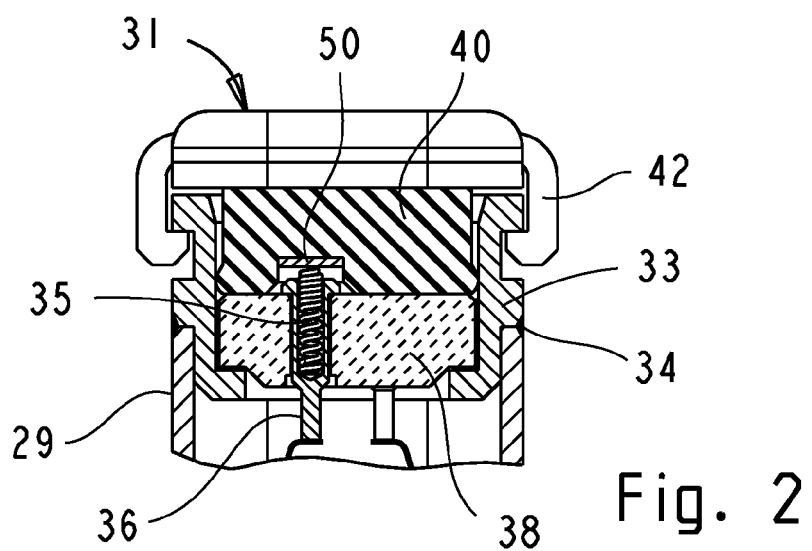
FIG. 2 is a partial cross-sectional view of the pressurized connector of FIG. 1, taken as indicated by the lines 2-2 of FIG. 1.

When connector is assembled as shown in FIG. 2, it is pressurized, i.e., compressible contacts 35 are compressed to provide contact pressure and the seals on lead terminal body 40 are compressed between pressure plate 44 and dielectric substrate 38 to provide sealing. When contacts 35 are compressed they electrically connect the corresponding lead contacts 50 to feedthrough pins 36, which extend into the interior of case 28 and connect to the electronics (not shown) inside device case 28. Concurrent with contact pressurization, the integral seals on the lead terminal body are compressed to seal the terminal body against the exterior surface of dielectric substrate 38 (interfacial seal) and against side walls 39 of the feedthrough cavity (peripheral seal). This seal system isolates the adjacent and non-common electrical connections from each other and from other conductive components, such as housing 33, and protects the connector interface from ingression of body fluids, which also tend to be conductive.

Figure 3:
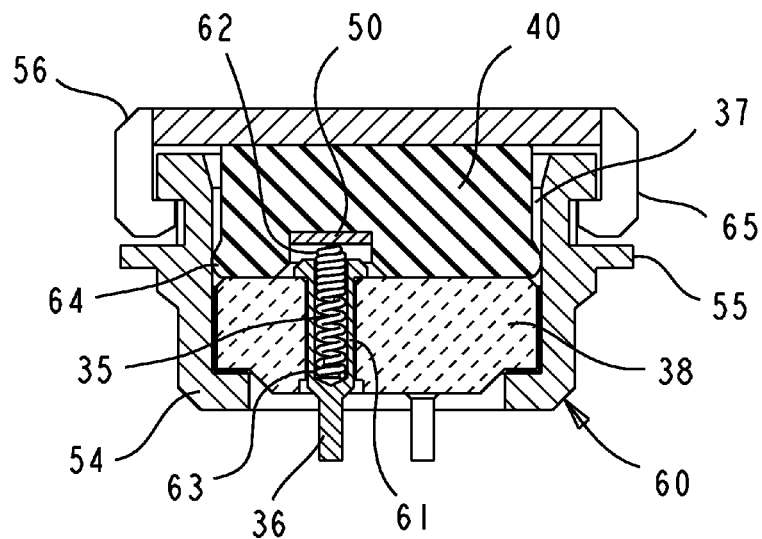
FIG. 3 is a cross-sectional view of a variation of the connector shown in FIG. 2, with a planar welding flange and alternate clamping means.

FIG. 3 shows a connector assembly with the same contact system, feedthrough cavity, and lead terminal as shown in FIG. 2. For illustrative purposes, feedthrough housing 54 has a welding flange 55, adapted for attaching the feedthrough on a face (rather than on an edge) of the device's case. After attachment, welding flange 55 becomes coplanar with the large surface of the case (not shown). Also in this embodiment, an alternative connector clamping means—a pressurization spring 56—is shown, which can be used interchangeably with the clamping cover described in connection with FIG. 2.

Feedthrough assembly 60 comprises dielectric substrate 38, housing 54, and feedthrough pins 36. These components are made from biocompatible materials, assembled as shown in FIG. 3, and joined by brazing using a biocompatible braze. The medical feedthrough materials and assembly techniques are well known in the art and are discussed in more detail in published US Patent Application 2007/0134985 A1 to Frysz et al. Currently preferred but non-limiting examples of materials include Ti and Ti alloys for the housing, highly purified aluminum oxide (pure alumina ceramic) for the dielectric substrate, platinum and platinum-iridium alloys for the feedthrough pins, and pure gold for brazing.

The contact system and its advantages will be now described in more detail. Feedthrough pin 36 has a tubular section 61, into which compressible contact 35 is installed. The tubular section of the pin resides substantially within the thickness of dielectric substrate 38, in which the pin is hermetically sealed. The tubular section can be obtained by drilling a blind hole in the feedthrough pin. Alternatively, the feedthrough pin can be a deep-drawn part or can be made out of tubing with one end hermetically sealed by crimping and/or welding. Compressible contact 35 is a miniature coil spring, and is protectively confined in tubular section 61. Only outer tip 62 extends from the tubular section to assure necessary contact compliance or deflection when connector is mated.

If the designer prefers to use a longer compressible contact, e.g., to increase contact deflection range or to further reduce compressible contact radial dimensions, the tubular section can be extended beyond the interior side of the dielectric substrate (into the device interior), without increasing the overall height of the connector. The compressible contact extension from the tubular section or the elevation of the contact tip above the exterior surface of dielectric substrate need not change when the contact spring is made longer. The coil spring contact has a variable pitch and a variable outside diameter. An outer end 62 of coil spring contact 35 is tightly wound to form a contact tip. The tightly wound top coils can be further joined together (e.g. by welding) or reinforced by adding a rigid tip insert. An opposite inner end 63 of the coil spring may have at least one coil with an outside diameter slightly larger than the inside diameter of the tubular section so that the coil spring can be pressed into the tubular opening of the feedthrough pin and retained therein by the radial interference. Alternatively, the inner end (near the bottom) of the tubular opening can have a necking or a slightly reduced diameter to provide an interference fit with the inner end of the contact spring.

The compressible contact can be made using known equipment and manufacturing techniques employed in fabrication of miniature coil springs for pogo pins used in electrical test sockets. The miniature coil spring can be made from a high strength biocompatible alloy, such as 80Pt-20Ir platinum-iridium alloy, which can be drawn into a high strength fine wire with a good formability.

Feedthrough 60 has cavity 37, formed by the exterior side of dielectric substrate 38 and the inside walls of the feedthrough housing 54. This cavity accommodates flat lead terminal 33 (FIG. 1) having body 40. Terminal 35 has an array of lead contact pads 50, which are the termini of the respective lead conductors. The lead body is molded from a medical silicone polymer, so that it can provide integral seal features. The lead contacts are recessed in lead terminal body 40 to allow the bottom surface of the terminal body to serve as a seal against the exterior surface of dielectric substrate 38. In addition to the inter-facial seal against the substrate surface, the sides of the terminal body can provide a perimeter seal against feedthrough cavity side walls. Integral rib 64 can be added to the side perimeter of the terminal body to enhance the peripheral seal. Similarly, the bottom sealing surface of the terminal body may have ribs or rings to optimize seal effectiveness and/or to lower the required seal compression force. The integral seals are preferred, but a separate seal, interposed between the body of the lead terminal and the exterior surface of the dielectric substrate, can be used instead.

When the terminal is inserted into the feedthrough cavity, the compressible contacts align with the respective lead contacts of the lead terminal. Preferably, the terminal is inserted into the feedthrough cavity with a slight interference, which initiates the peripheral seal and securely retains the terminal in the feedthrough cavity for the remaining assembly steps.

Figures 4A, 4B:
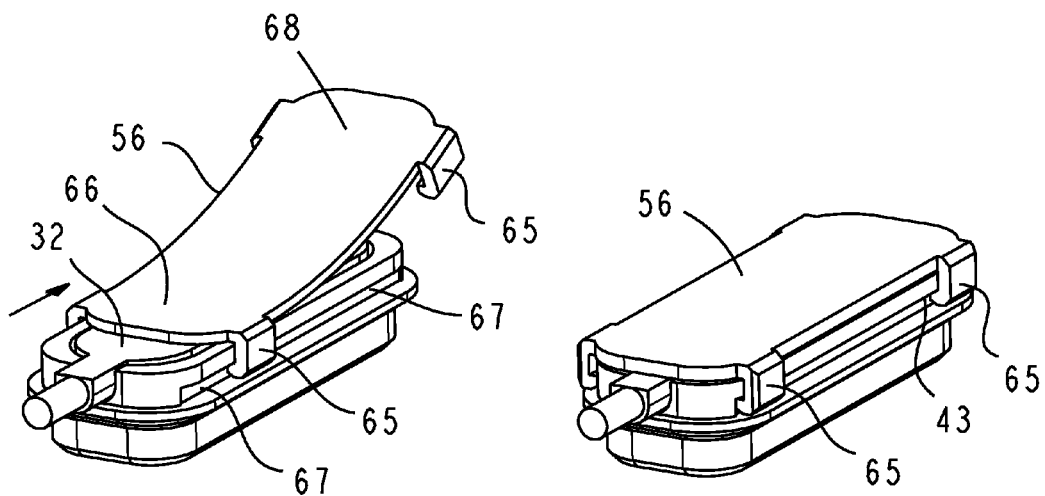
FIG. 4A is a perspective view of the connector of FIG. 3 with a pressurization spring partially engaged.
FIG. 4B is a perspective view of the connector of FIG. 3 with the pressurization spring fully engaged.

Pressurization spring 56 with engagement latches 65 can be applied as shown in FIGS. 4A and 4B. First, a pair of latches 65 on the first (front) end 66 of the clip is engaged with grooves 67 from the front end of the feedthrough. After sliding the retention spring toward back in the direction of the arrow to the position shown in FIG. 4A, a second (back) end 68 of the spring is pressed down until the other two latches line up with grooves 67 on the back side of the feedthrough. The spring is then pushed toward front to the final position shown in FIG. 4B. As the spring is engaged against undercuts 43 formed by grooves 67, the spring exerts pressure against top surface of lead terminal body 40, forcing the lead terminal contact pads to make pressure connections with the corresponding compressible contacts and concurrently compressing the seals.

The spring can be made from a high strength biocompatible alloy such as titanium alloy 6Al-4V. The top surface of the lead terminal body on which the retention spring slides may incorporate a low-friction polymeric lining or a coating, such as a poly-para-xylylene (sold under the trademark Parylene by Specialty Coating Systems, Indianopolis, Ind.), to reduce sliding friction between the two components.

The connector's small size is attained by confining the compressible contact in the tubular section of the feedthrough pin, so that the compressible contact resides substantially within the thickness of the dielectric substrate, defined by the exterior and interior sides or surfaces of the substrate. The compressible contact can thus be made longer in order to reduce the contact's radial or cross-sectional dimensions without impacting connector height. The small radial dimensions of the compressible contacts and the small effective contact height (the elevation above the exterior surface of the dielectric substrate) enable low profile connectors with closely spaced contacts. A large number of connections can thus be provided in a small connector volume. The exemplary device shown in FIG. 1 can be less than 5 mm thick and the total height of the connector assembly, including the feedthrough, can be less than 4 mm.

FIGS. 5-10—First Embodiment for Leads with Iso-Diametric Terminals

Figure 5:
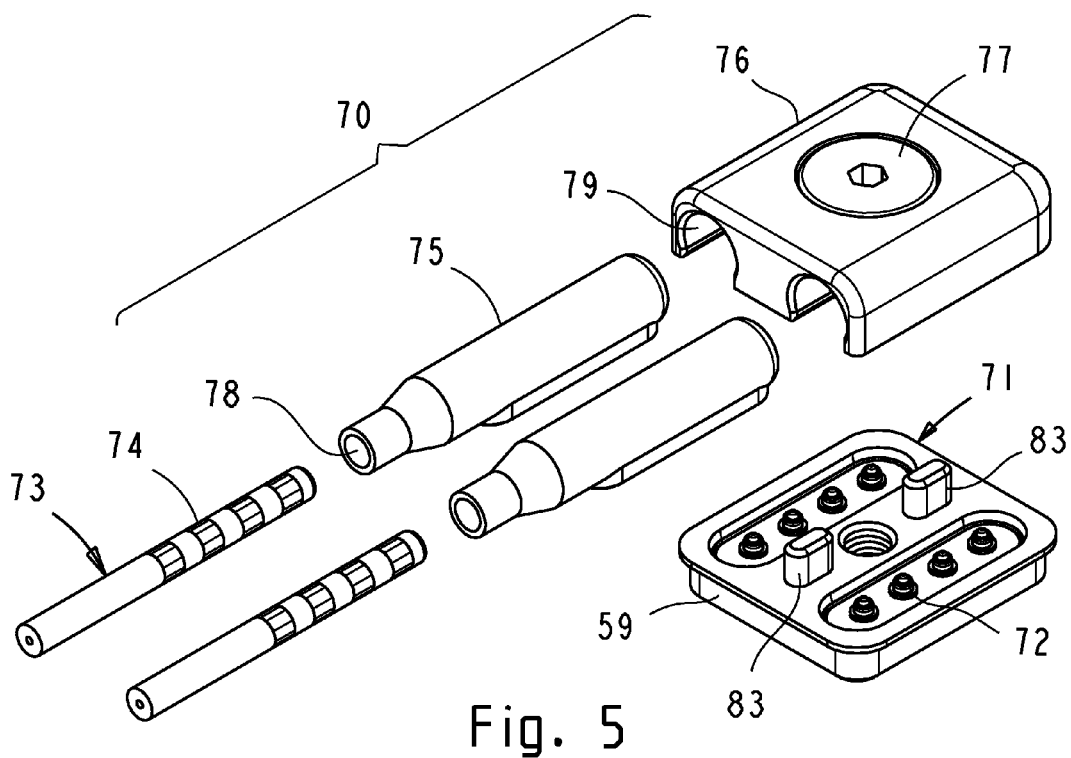
FIG. 5 is an exploded perspective view of an embodiment of the connector for connecting iso-diametric leads where lead terminals are pre-inserted into the seals and subsequently inserted into the cover where they are retained prior to connector pressurization.

FIG. 5 shows an exploded perspective view of an implantable connector 70 for leads with iso-diametric proximal terminals. This connector has (a) compressible contacts integrated with feedthrough pins; (b) a seal into which the lead terminal is inserted without significant interference, (c) a cover and/or a feedthrough cavity into which the lead-seal assembly is inserted with or without interference; and (d) a clamping or pressurization means such as a clamping cover secured to the feedthrough housing with a clip, a latching spring, or a screw.

Connector 70 has a hermetic feedthrough assembly 71 with compressible contact assemblies 72, lead end terminals 73 with lead contacts 74, seals 75, a pressurization cover 76, and a clamping screw 77.

In this embodiment, the lead-seal assembly is preassembled in the clamping cover prior to connector pressurization. The clamping cover can be fabricated from a biocompatible material such as titanium or titanium alloy or a hard polymer such as polyetheretherketone PEEK, preferably reinforced (e.g. filled with carbon fibers to increase strength and stiffness). Implantable-grade PEEK, also known as PEEK-OPTIMA is available from Invibio, Inc. Ceramic materials such as pure alumina or toughened alumina are also suitable cover materials.

A desirable method of assembly of connector 70 is to first insert each lead terminal into circular lumen 78 of respective seal 75 without significant interference (preferably with less than 1 Newton (N) axial insertion force). Once the lead is protected in the seal, the lead-seal assembly is inserted into channel 79 in cover 76, preferably with a slight interference, to obtain a lead-seal-cover assembly 80 shown in FIG. 6. The retention of the lead-seal assembly in the cover by the slight interference fit prevents inadvertent dislocation of the lead in the cover assembly. In addition, the profile of the channel is a-shaped, with narrowing at 81. This further prevents dislodging of the lead-seal assembly in the radial direction. These retention features are advantageous since they assure secure holding of the components in the cover through the remaining assembly steps. The lead contact registration in the cover assembly can be visually verified via seal apertures 82 and reliably maintained.

An additional advantage of the present assembly method is that the radial pressure from the interference fit between the lead-seal assembly and the cover is communicated to the lead-seal interface and thus initiates the seal between lead electrode contacts. The initial seal preload excludes fluids from critical seal areas during connector installation and reduces the total clamping force required for connector pressurization.

In the final assembly step, the lead-seal-cover assembly is aligned with feedthrough 71 using alignment bosses 83 in feedthrough housing 59 and the corresponding slotted holes 84 in cover 76. The connector is fully mated by clamping cover 76 to feedthrough housing 59 with screw 77. The assembled connector is shown in FIG. 7.

Figures 6, 7:
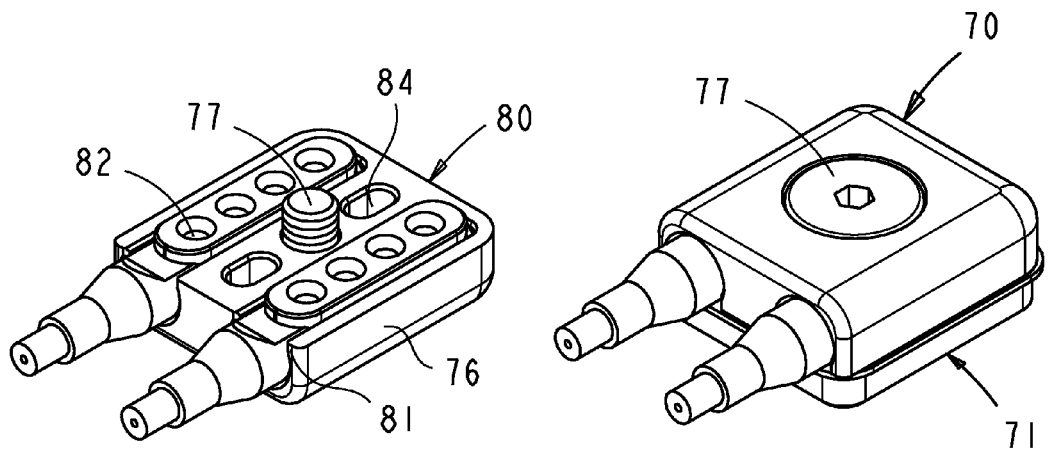
FIG. 6 is a perspective view of the connector cover with the lead-seal assembly installed.
FIG. 7 is a perspective view of the fully assembled (pressurized) connector of FIG. 5.
Figure 8:
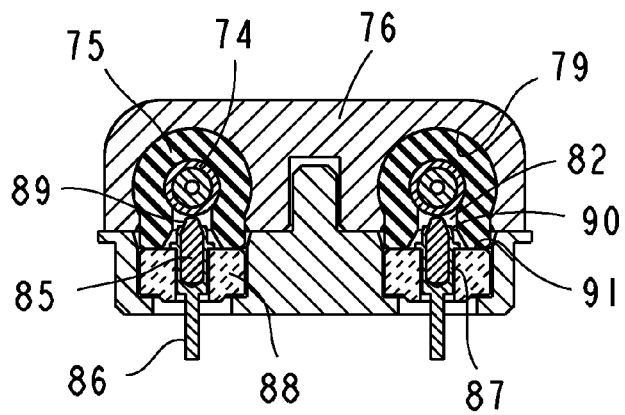
FIG. 8 is a cross-sectional view of the connector of FIG. 7 taken through the contacts, in a plane normal to the leads, as indicated by the line 8-8 of FIG. 9.

FIG. 8 is a cross-sectional view of the mated connector of FIG. 7, taken through the contacts, in the plane normal to the lead.

The connector uses compressible coil spring contacts 85 (similar to contact 35 of FIG. 3). Alternatively, a conductive button such as a platinum-iridium fuzz button, or a metal-particle-filled conductive elastomer button can be used. The compressible contact is enclosed in tubular section 87 of feedthrough pin 86. The tubular section of the pin resides substantially within the thickness of dielectric substrate 88 in which the pin is hermetically sealed. The compressible contact has a tapered outer end 89 and can be retained in the tubular section by a rolled or crimped rim 90 at the top of the tubular section. The rim is rolled or crimped after the compressible contact is inserted into the tubular section. Alternatively, an inwardly rolled rim can be pre-fabricated prior to the feedthrough assembly to allow a compressible button to be forced through the rim and snap-back in the tubular section.

The compressible contacts electrically connect lead contacts 74 to the corresponding feedthrough pins 86 which, in turn, connect to the device's electronics contained in the device's case (not shown). The compression of the seals between the inner surfaces of cover channels 79 and exterior surface 91 of dielectric substrate 88 completes electrical isolation between adjacent contacts and isolates the contacts from other non-common conductive components and from ambient body fluids or fluids that may be used to rinse the implantable components intra-operatively.

Figure 9:
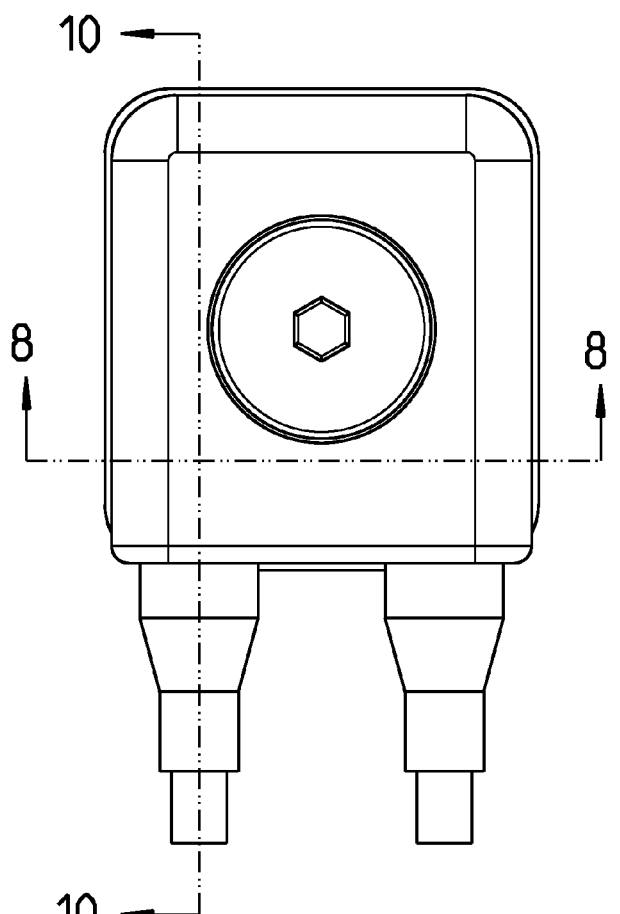
FIG. 9 is a top view of the connector of FIG. 7.
Figure 10:
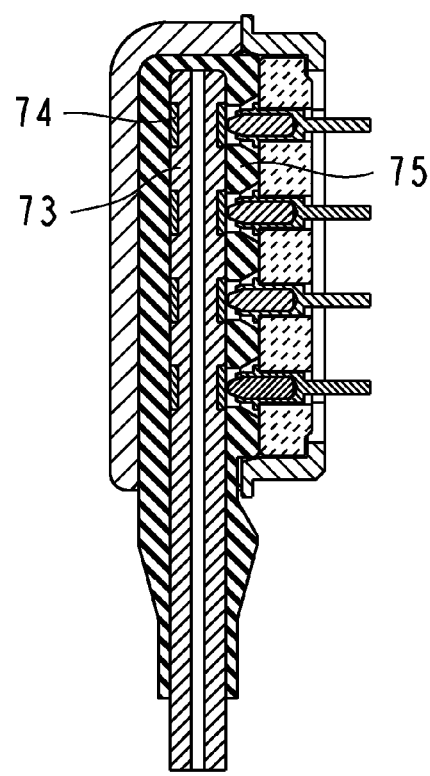
FIG. 10 is a cross-sectional view of the connector of FIG. 7 taken through contacts, along the lead axis, as indicated by the line 8-8 of FIG. 9.

FIG. 9 is a top view of the connector of FIG. 7, which serves as a reference for the cross-sectional views of FIGS. 8 and 10.

FIG. 10 is a cross-sectional view of the assembled connector of FIG. 9, taken along the lead. This view illustrates how inter-contact seal between adjacent contacts is accomplished by compressive radial pressure on seal 75 around the insulated portion of lead 73, between tubular contacts 74.

Figure 11:
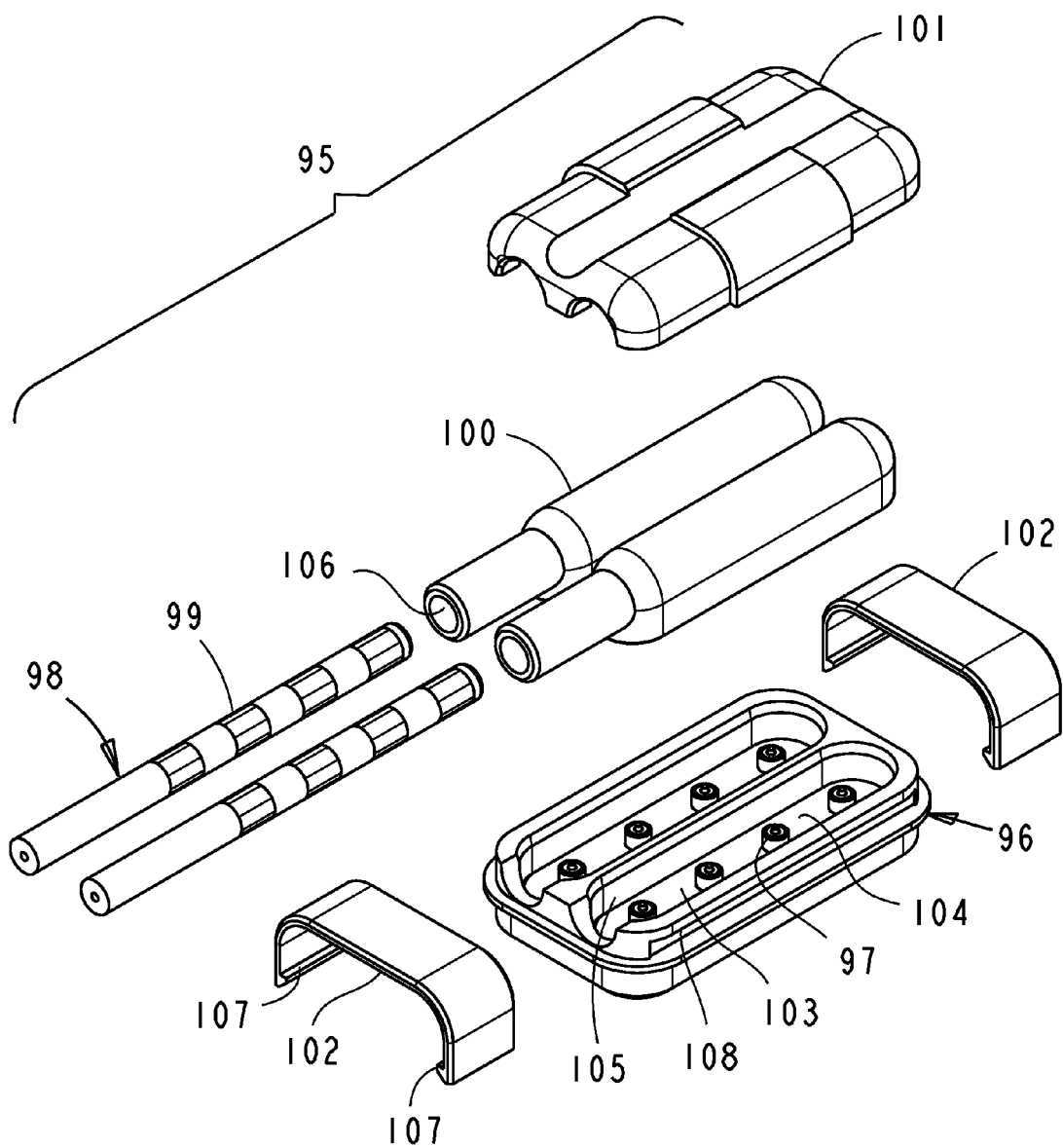
FIG. 11 is an exploded perspective view of the connector for iso-diametric leads, where lead terminals are pre-inserted into the seals and subsequently inserted into the feedthrough cavity prior to connector pressurization.
Figure 12:
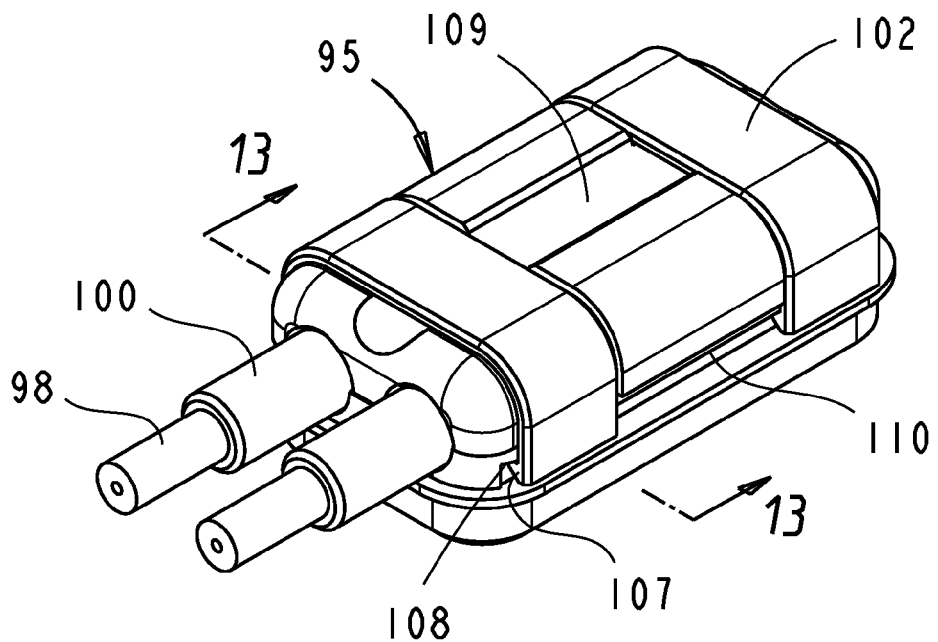
FIG. 12 is a perspective view of the fully assembled (pressurized) connector of FIG. 11.
Figure 13:
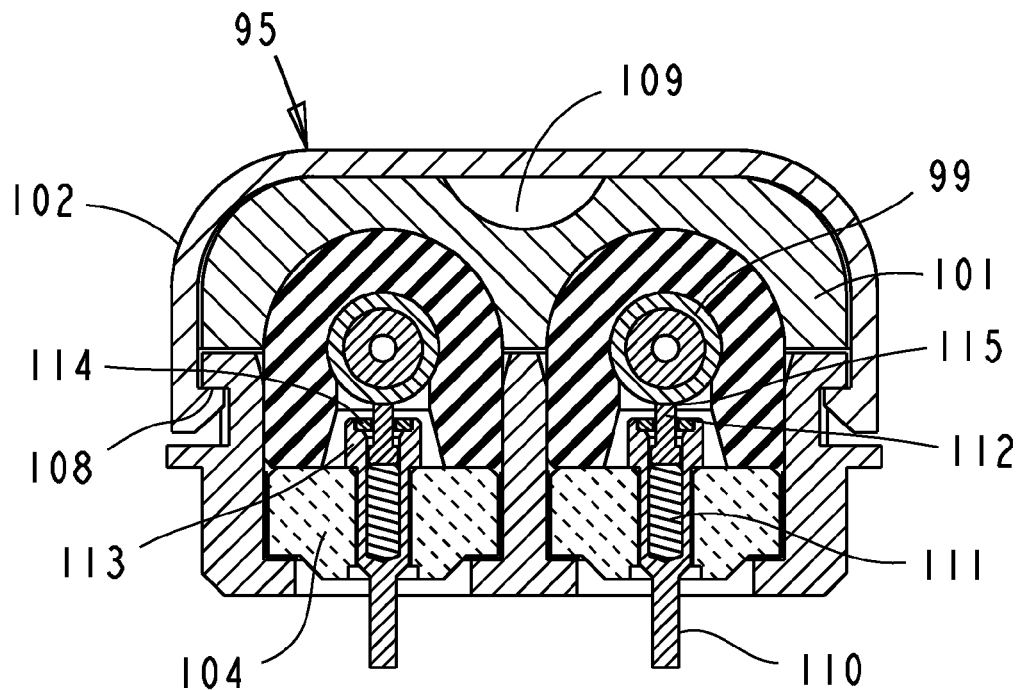
FIG. 13 is a cross-sectional view of the connector of FIG. 12, taken through the contacts, in the plane normal to the leads, as indicated by the line 13-13 of FIG. 12.

FIGS. 11-13—Second Embodiment for Leads with Iso-Diametric Terminals

FIG. 11 is an exploded perspective view of a connector 95 which has a hermetic feedthrough assembly 96 with compressible contact assemblies 97, lead terminals 98 with tubular contacts 99, seals 100, a clamping cover 101, and U-shaped retention clips 102. The feedthrough has a cavity 103, bound by the surface of a dielectric substrate 104 and inside walls 105 of the feedthrough housing.

In order to assemble connector 95, the proximal terminal of each lead 98 is first inserted into a respective circular lumen 106 of seal 100 without significant interference (preferably less than 1 N axial insertion force). Once the lead terminal is protected by the seal, the lead-seal assembly is inserted into feedthrough cavity 103, preferably with slight interference. The slight interference is advantageous since it assures secure holding of the lead-seal assembly in the feedthrough cavity through the final steps of connector assembly. In addition, compression of the seal in the feedthrough cavity initiates inter-contact and peripheral seals. Thus obtained feedthrough-seal-lead assembly is pressurized by securing clamping cover 101 with clips 102. Clip latches 107 cooperate with undercuts 108 on the outside of the feedthrough housing to maintain connector pressurization.

FIG. 12 is a perspective view of the fully assembled connector 95. Retention clip latches 107 engage undercuts 108 on the sides of the feedthrough housing, thus maintaining connector in the pressurized or mated state. Relief cut 109 on the top of the clamping cover can be used for insertion of a stylet (to increase tension on the clip) and/or for aiding in removal of clips with a surgical tool.

If desired, a simple clamping tool (not shown) can be used to temporarily clamp the connector in order to facilitate installation and/or removal of the clips. Feedthrough undercuts 108 can be extended throughout feedthrough housing length (as shown) so that the temporary clamping tool can engage the feedthrough undercuts at mid-sections 110 and force the cover down with a quick action screw or cam.

FIG. 13 is a cross-sectional view of the mated connector of FIG. 12 taken through the contacts in the plane normal to the lead. Compressible contact 111 is a coil spring or a conductive button such as a fuzz button or a metal-particle-filled elastomer button. Rigid conductive insert 112 provides the contact tip (contact point) for connecting to the lead tubular contact. The compressible contact and the rigid conductive insert are retained in the tubular section of the feedthrough pin by a washer-like insert 114, attached to the top of a feedthrough pin collar 113, preferably by laser welding. The compressible contact is preloaded (pre-compressed) by insert 114 to provide desirable contact characteristics (lower contact force variation). Alternatively the rim can be made thinner so that it can be crimped or rolled inwardly (as is rim 90 in, FIG. 8) to retain the compressible contact and the rigid tip insert under internal preload.

In addition to providing a more consistent contact force, this implementation of the contact provides a robust contact tip 115. The rigid tip can be flat, rounded, or tapered, and may have one or more surface cuts, such as V-slots, to provide pointed contact features for a low resistance connection with lead contact 99.

Figure 14:
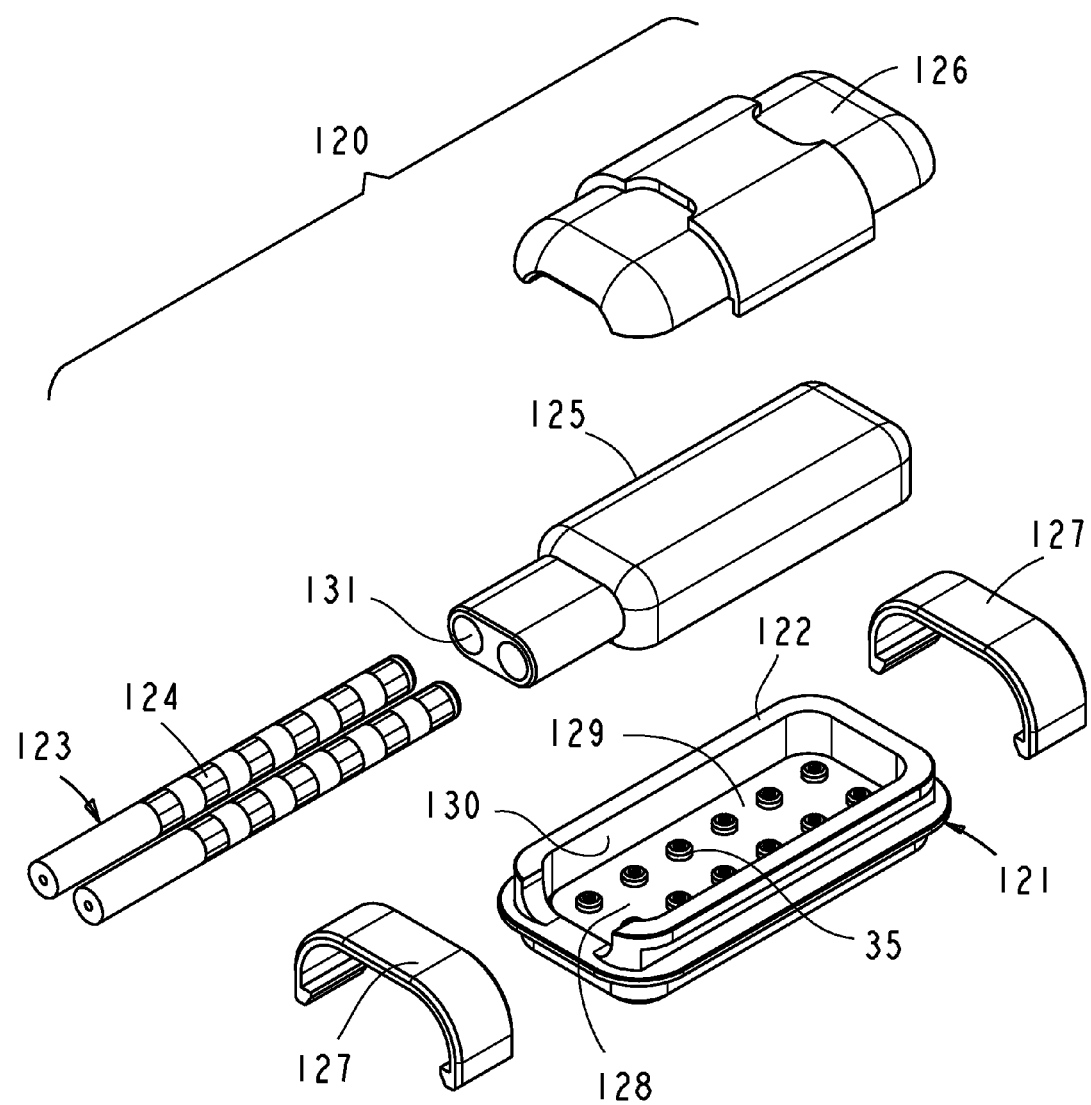
FIG. 14 is an exploded perspective view of the connector with a dual-lead seal and a single feedthrough cavity.
Figure 15:
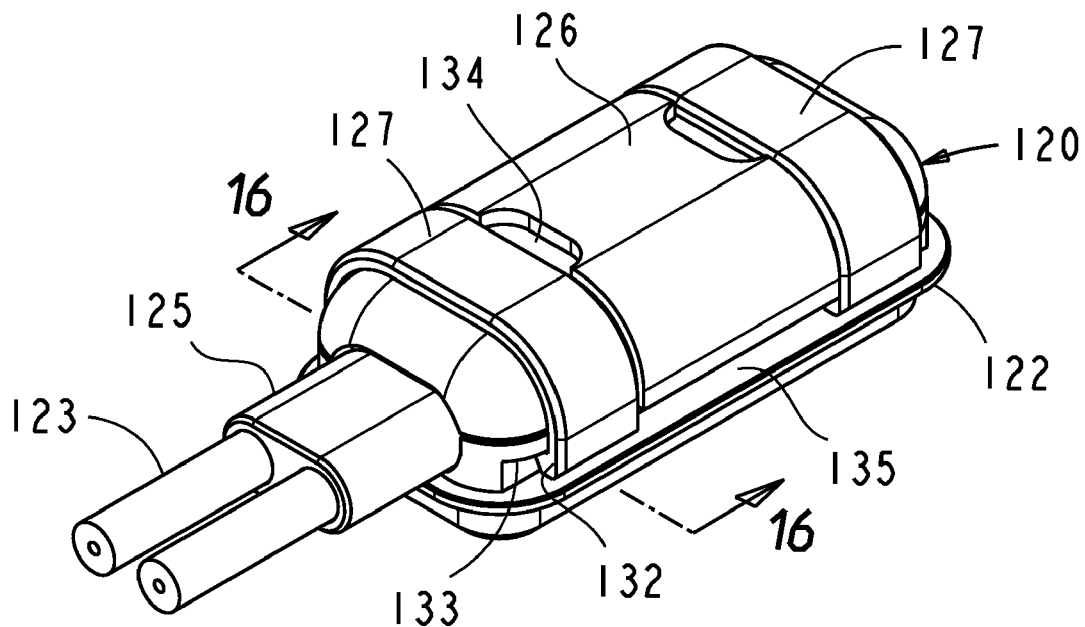
FIG. 15 is a perspective view of the fully assembled (pressurized) connector of FIG. 14.
Figure 16:
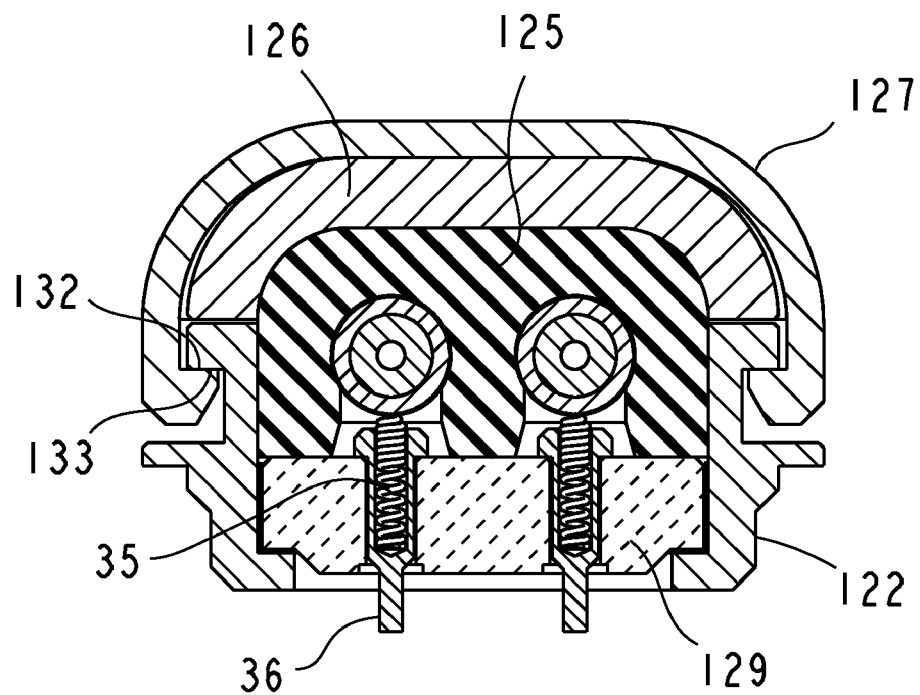
FIG. 16 is a cross-sectional view of the connector of FIG. 15, taken through the contacts, in a plane normal to the leads.

FIGS. 14-16—Third Embodiment for Leads with Iso-Diametric Terminals

FIG. 14 is an exploded perspective view of connector 120, which has hermetic feedthrough 121 with compressible contacts 35, lead terminals 123 with contacts 124, seals 125, clamping cover 126, and retention clips 127. The feedthrough has an exterior cavity 128, bound by top surface of a dielectric substrate 129 and inside walls 130 of a feedthrough housing 122. These are the same functional components as in connector 95 of FIG. 11 and the same assembly method is applicable. However, while connector 95 has a separate seal for each lead and a separate feedthrough cavity for each seal-lead assembly, connector 120 has a single seal 125 with two lead-receiving lumens side-by-side so that two leads are accommodated in a single seal. Each lead terminal 123 is received into respective seal lumen 131, and the dual lead-seal assembly is accommodated in a single feedthrough cavity 128. These and other differences, such as contact design, number of contacts per lead, and contact spacing, illustrate how these features can be used interchangeably in various connector embodiments.

FIG. 15 is a perspective view of the fully assembled connector 120. Retention clip latches 132 engage undercuts 133 on the outside of the feedthrough housing 122, thus maintaining the connector in the mated state. Relief cuts 134 on the top of clamping cover 126 can be used for aiding in removal of clips with a screwdriver a surgical tool.

If desired, a simple clamping tool (not shown) can be used to temporarily clamp the connector in order to facilitate installation and/or removal of the clips. Feedthrough undercuts 133 continue along the feedthrough length so that the latches of the temporary clamping tool could engage the feedthrough undercuts at mid-sections 135 and force the cover down with a quick action screw or cam. After the retention clips are installed the temporary tool is removed.

FIG. 16 is a cross-sectional view of the mated connector of FIG. 15 taken through the contacts in the plane normal to the lead. Compressible contact 35 is a coil spring retained in feedthrough pin 36 as described earlier.

FIGS. 17-22—Additional Embodiments for Leads with Iso-Diametric Terminals

Figure 17:
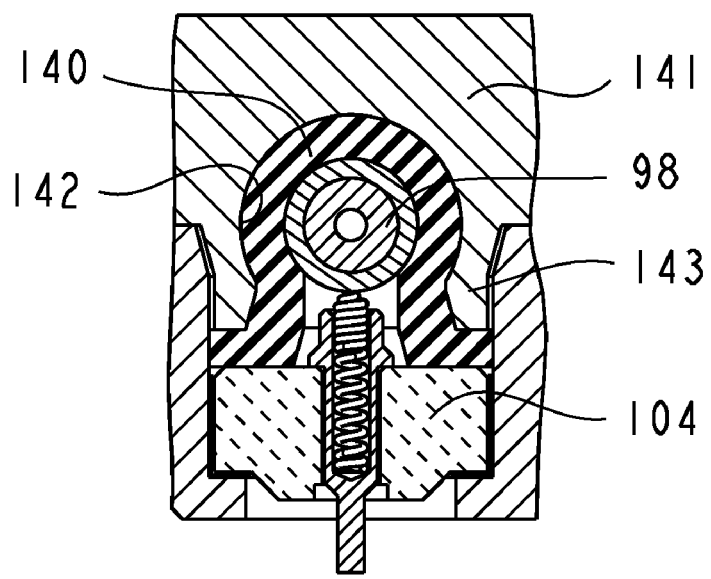
FIG. 17 is a variation of cross-sectional view of FIG. 13, taken as indicated by the lines 13-13 of FIG. 12, where an Ω-profiled seal is retained in cover protrusions extending into the feedthrough cavity.

FIG. 17 is a partial cross-sectional view of a mated connector, which is a variation of the connector shown in cross-sectional view of FIG. 13. The assembly of lead terminal 98 and a Ω-profiled seal 140 is retained in a complementarily profiled channel 142 in cover 141. The cover has protrusions 143 extending into the feedthrough cavity, which guide the cover assembly into the feedthrough during assembly and pressurization.

Figure 18:
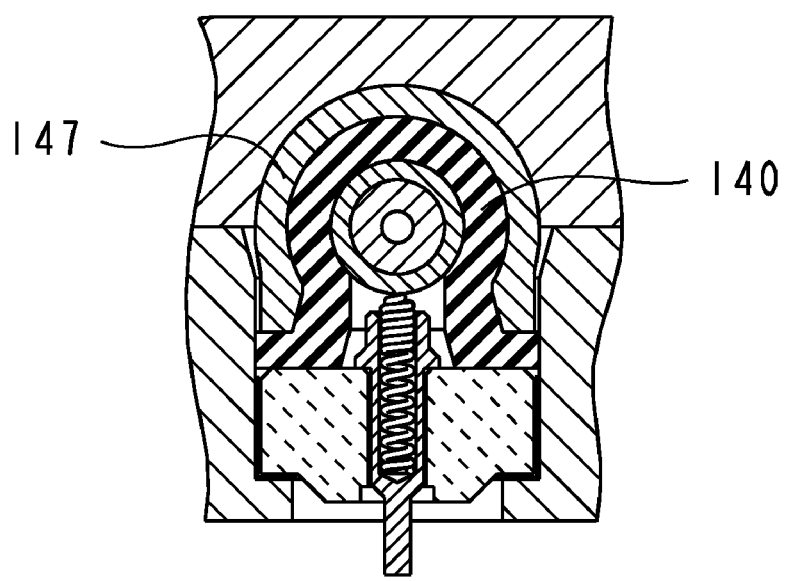
FIG. 18 is a variation of cross-sectional view of FIG. 17 where the Ω-profiled seal is retained in a C-profiled springy sleeve.

FIG. 18 is a variation of the connector shown in cross-sectional view of FIG. 17. The assembly of lead terminal 98 and Ω-profiled seal 140 is inserted into a C-profiled spring sleeve 147 prior to insertion into the feedthrough cavity. The spring sleeve activates the inter-contact seals prior to full connector pressurization. Pre-pressurization of the inter-contact seal by the spring sleeve reduces the pressurization load that needs to be applied through the cover.

FIGS. 19 through 22 show additional embodiments of compressible contacts which can be used interchangeably with those already discussed.

Figure 19:
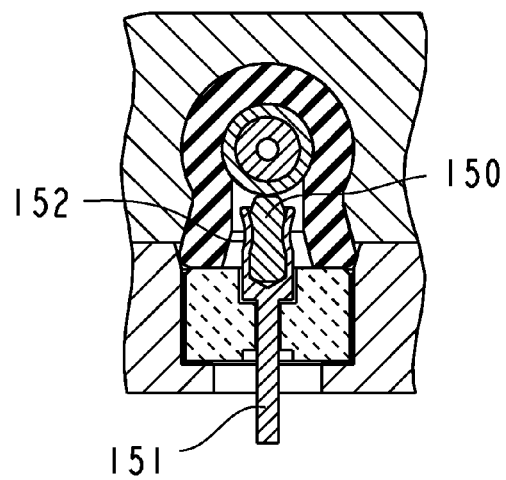
FIG. 19 is a variation of cross-sectional view of FIG. 8, taken as indicated by the lines 8-8 of FIG. 9, where the compressible contact is a conductive button retained in a profiled tubular opening of the feedthrough pin.

FIG. 19 is a partial cross-sectional view of a connector which is a variation of the connector shown in cross-sectional view of FIG. 8. A compressible contact 150 can be a fuzz button or a metal-particle-filled elastomer button. The compressible conductive button is protectively confined and retained in a profiled tubular section 152 of a feedthrough pin 151. The tubular opening has an hourglass profile which helps to retain the contact by compressing the contact at the narrow diameter necking and allowing the contact to expand at the larger diameter below.

Figure 20:
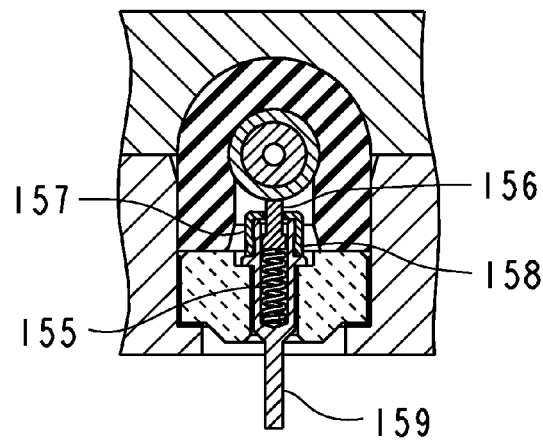
FIG. 20 is a variation of cross-sectional view of FIG. 13, taken as indicated by the lines 13-13 of FIG. 12, where the compressible contact is a coil spring, secured and preloaded by a cylindrical hat attached to the feedthrough pin.

FIG. 20 is a partial cross-sectional view of a connector which is a variation of the connector shown in cross-sectional view of FIG. 13. The contact assembly includes a compressible coil spring 155 (or alternatively a fuzz button) used with a rigid conductive tip insert 156. The compressible contact and the tip insert are retained by a hat 157 attached to the feedthrough pin by crimping, snap-on feature, biocompatible adhesive, or a combination thereof. For a snap-on attachment, the hat may have at least one dimple 158 that retains the hat against undercut in the corresponding area of a feedthrough pin 159. The rigid conductive insert provides a robust contact tip for connecting to the lead's tubular contact. The compressible contact can be preloaded (pre-compressed) by'hat 157.

Figure 21:
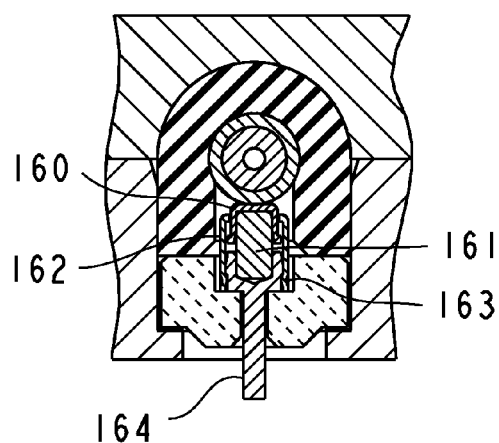
FIG. 21 is a variation of cross-sectional view of FIG. 13, taken as indicated by the lines 13-13 of FIG. 12, where the compressible contact is a conductive button or a coil spring, secured and preloaded by a cylindrical hat attached to the feedthrough pin.

FIG. 21 is a variation of the connector shown in FIG. 20 where a larger diameter compressible contact can be accommodated. A rigid (non-resilient) conductive tip insert 160 is a drawn or machined part that partially encloses and protects the compressible contact 161. The compressible contact and the rigid contact tip are further protected and retained by hat 162 attached to the feedthrough pin using a snap-on feature and/or adhesive. For a snap-on attachment, hat 162 may have at least one dimple 163 that retains the hat against an undercut in the corresponding area of a feedthrough pin 164. The compressible contact can be preloaded (pre-compressed) by hat 162

Figure 22:
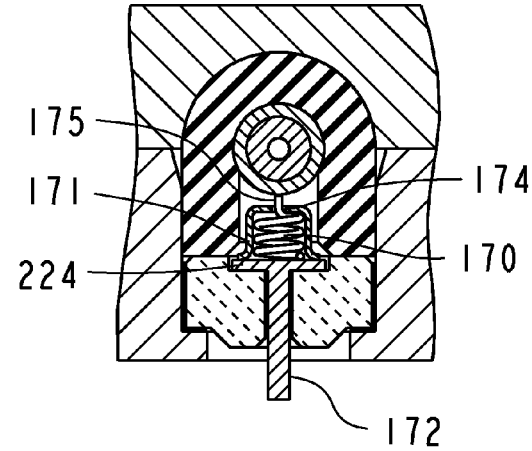
FIG. 22 is a variation of cross-sectional view of FIG. 21, taken as indicated by the lines 13-13 of FIG. 12, where the compressible contact is a coil spring, protectively confined in a hat welded to the feedthrough pin.

FIG. 22 is a variation of the connector shown in the cross-sectional view of FIG. 21 where the compressible contact is a coil spring 170, which is protectively confined in a cylindrical hat 171 attached to a nail-head 172 of a feedthrough pin 173, preferably by welding. A pilot hole 174 on the top of the hat precisely positions and guides contact tip 175 on the spring's outer end, to assure mating alignment to the lead's tubular contact. The contact spring can also be pre-loaded by the hat.

Figure 23:
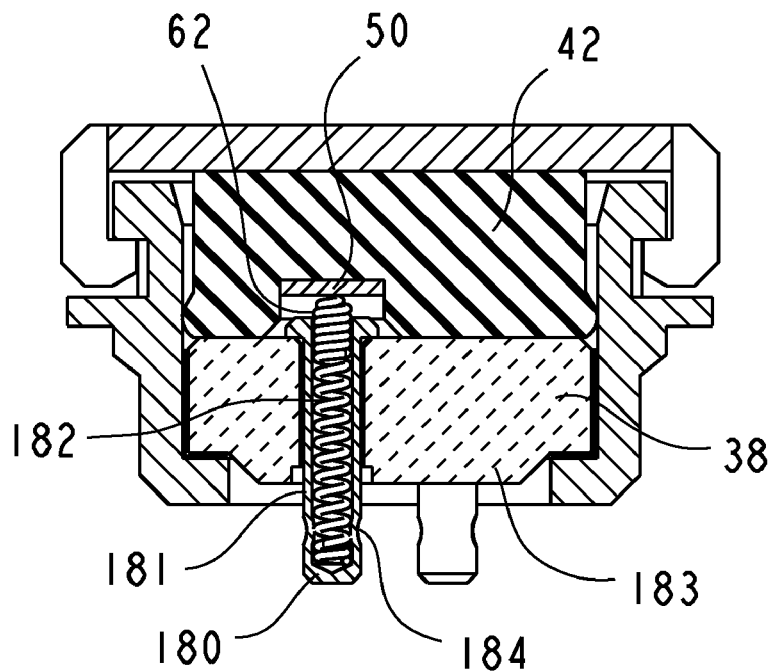
FIG. 23 is a variation of the cross-sectional view of FIG. 3, taken as indicated by the lines 2-2 of FIG. 1, where the tubular section of the feedthrough pin and the compressible contact extend beyond the bottom side of the dielectric substrate and are crimped together from the feedthrough interior side.
Figure 24:
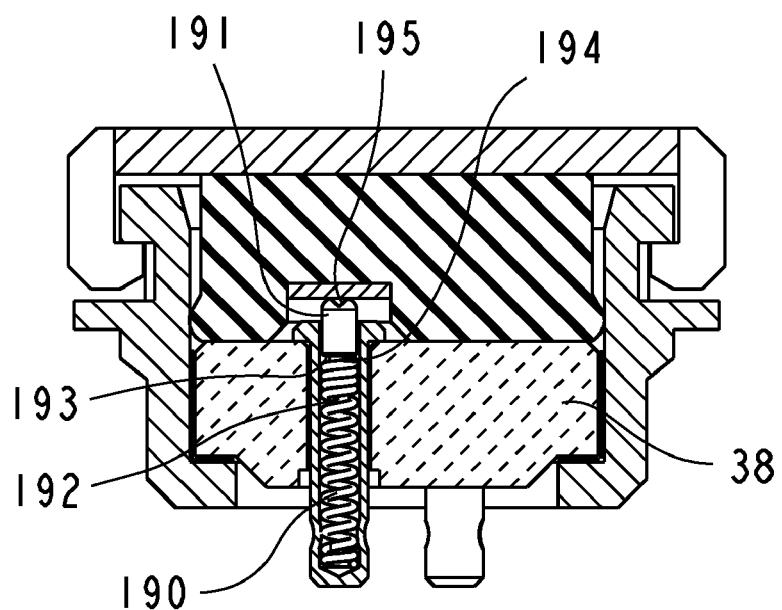
FIG. 24 is a variation of the connector of FIG. 23 where the compressible contact has a rigid contact tip provided by a conductive contact insert attached to the outer end of the coil spring.

FIGS. 23-24 Additional Embodiments for Leads with Flat Contact Terminals

FIG. 23 is a partial cross-sectional view of a variation of the connector shown in the cross-sectional view of FIG. 3 with an alternate compressible contact embodiment. A tubular section 181 of a feedthrough pin 180 and a compressible contact 182 extend beyond the interior side 183 of dielectric substrate 38 (the side that is in the interior of the device case after feedthrough is attached to the device's case). The tubular section can be crimped as shown at 184 to retain the compressible contact in the tubular section and to enhance electrical connection between the compressible contact and the feedthrough pin. This contact embodiment also demonstrates how a long, high-compliance compressible contact can be employed without increasing connector height.

FIG. 24 is a variation of the connector shown in FIG. 23 where a compressible contact 190 has a rigid conductive tip insert 191, attached to the outer end of the coil spring. The tip insert is a stepped diameter round pin, with a larger diameter tip 191 and a smaller diameter shank 192 (obscured by the spring coils). The tip diameter is sized for a free movement within the tubular opening of the feedthrough pin, and it generally matches the outside diameter of the coil spring. The smaller diameter shank is sized for a snug fit inside the coil spring where it is inserted until a pin shoulder 193 rests on the outer end of the coil spring. The pin can be retained in the spring by an interference fit and/or attached to it, preferably by welding, as shown at 194 or just below.

The contact tip can further have at least one cut, such as a V-shaped slot 195, to provide pointed contact point features. Such features help in self-cleaning of the contact during mating and thus help to assure a low contact interface resistance at moderate contact loads.

Figure 25:
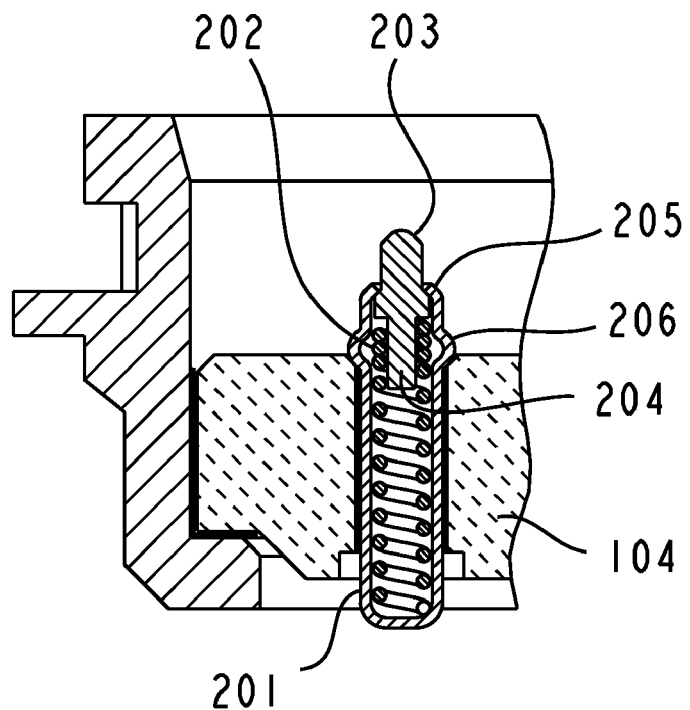
FIG. 25 is a cross-sectional detail of a feedthrough assembly showing a tubular pin confining a compressible contact with a rigid contact tip, where the outer end of the tubular pin is crimped to retain the compressible contact.
Figure 26:
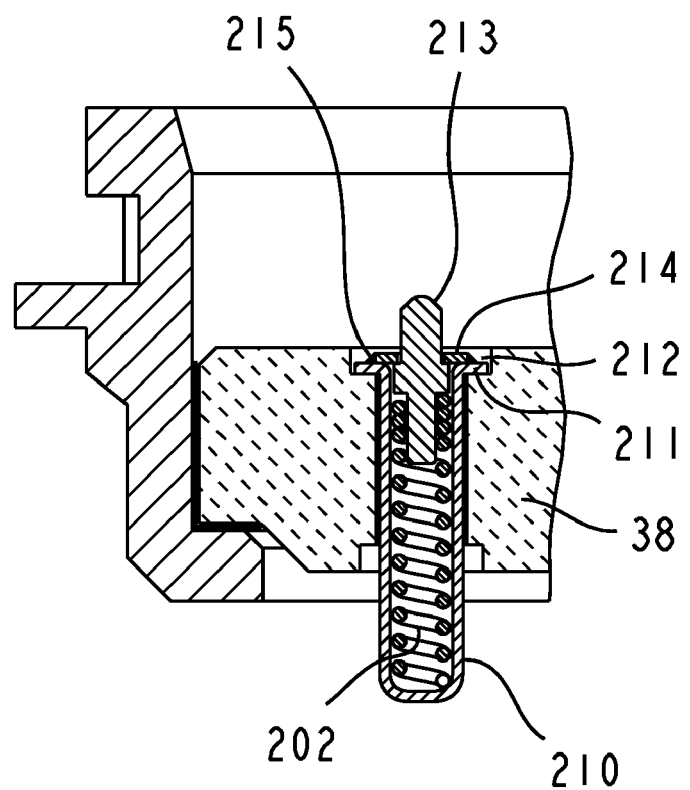
FIG. 26 is a cross-sectional detail of a feedthrough assembly showing a tubular pin confining a compressible contact with a rigid contact tip, where an insert is welded to a flange on the outer end of the tubular pin to retain the compressible contact.

FIGS. 25-26 Additional Embodiments of Compressible Contacts with Rigid Contact Tip FIGS. 25-26 are cross-sectional details of a feedthrough assembly showing additional embodiments of compressible contacts having a rigid contact tip. The tubular feedthrough pins are designed to be economically fabricated by deep drawing but can also be adapted for machining.

In the embodiment of FIG. 25, a tubular feedthrough pin 201 confines a coil spring contact 202 with a rigid contact tip 203. The necked portion 204 of the contact tip is accommodated in the outer end coils of the spring which may be tightly wound. The plunger may be optionally welded to the outer end of the coil spring. The outer end 205 of the tubular pin is crimped (rolled) to retain the compressible contact. The free length of spring 202 may be greater than the depth of the tubular opening in pin 201 so that the spring is preloaded when it is assembled as shown. A circumferential form 206 provides a positive stop for locating the pin in the dielectric substrate 104.

FIG. 26 is a cross-sectional detail of a feedthrough assembly showing a low profile embodiment of a coil spring contact with a rigid contact tip. A tubular feedthrough pin 210 has a flange 211 which seats on the bottom of a counterbore 212 on the outer side of the dielectric substrate. A rigid contact tip 213 is retained by an insert 214 which is welded to the flange at 215. Both flange 211 and insert 213 may reside within counterbore 212 so that only the contact tip extends beyond the exterior side of the dielectric substrate.

FIGS. 27-29 Coil Spring Contacts with a Hat Attached to Head of Feedthrough Pin FIG. 27 is a cross-sectional detail of a connector showing a coil spring contact 220 protectively contained in a tubular hat 221 wherein the top of the hat is conductively attached to the profiled head 222 of a feedthrough pin 223 by a weld 224. The outer end of the coil spring has a centrally extending filar 225 which provides the contact point.

The spring contact is pre-assembled with the hat and added to the brazed feedthrough assembly as shown in FIGS. 28A-B. The bottom 226 of the hat can be crimped to retain the spring contact and/or the inner end of the spring can be joined to the open end of the hat by a weld 227 (better seen in FIG. 29).

The head of the feedthrough pin has a substantially arcuate profile with a centrally disposed slot 228 which accommodates and guides filar 225. The top of the hat has a cutout 229 cooperating with the profiled outer end of the feedthrough pin. When the spring-hat assembly is fully seated in the counterbore 230 of the dielectric substrate 231, the top of the hat is co-planar with the top of the feedthrough pin and the complementary edges can be welded as shown in FIG. 28B. The spring contact is thus fully contained and can be preloaded within the hat in order to provide a consistent contact force. Filar 225 is centered and guided all around by the resulting opening.

FIGS. 30A-C Coil Spring Contacts Protected by Outer-End Head of Feedthrough Pin FIGS. 30A-C show a coil spring contact assembly wherein a coil spring contact 235 is installed directly over the head 222 of a feedthrough pin 236, i.e., without using a hat. The inner end 237 of the coil spring (seen on the inverted view of the spring in FIG. 30B) is formed toward the spring central axis so that it can snap into the undercut 238 of the feedthrough pin, thus retaining the spring. Counterbore 230 is sized to closely confine the spring contact. When the spring is compressed, the inner end of the coil spring makes direct pressure connection to a shoulder 239 of the feedthrough pin. A radial excursion of the outer end of the spring contact is limited by the head of the feedthrough pin.

FIGS. 31-34 Coil Spring Contacts with Extensions Tails Installed in Tubular Feedthrough Pins The coil spring contacts disclosed in these Figures have a centrally extending tail 241 on their inner end which can be installed into the tubular opening 242 of a feedthrough pin 243 to electrically interface and retain the contacts. Tail 241 may have a wavy shape to facilitate an interference fit or may be retained in opening 242 by other means such as a conductive adhesive or crimping the inner end of the tubular contact.

The contact spring is inserted into opening 242 until the innermost coil rests on the flange 244 of the feedthrough pin. This assures a redundant electrical connection when the contact is compressed.

FIGS. 31-32 shows a coil spring contact 245 protectively confined within a counterbore 230 on the exterior side of dielectric substrate 231.

FIG. 33 is a variation of FIG. 32 showing a coil spring contact 246 having a tapered outer end 247. The tapered spring coils are tightly wound to provide a robust contact point.

FIG. 34 is a variation of FIG. 32 showing a shallower counterbore 230 and additionally having a seal 247 which protectively confines the contact. This configuration can be used when a discrete seal is required.

Figure 37:
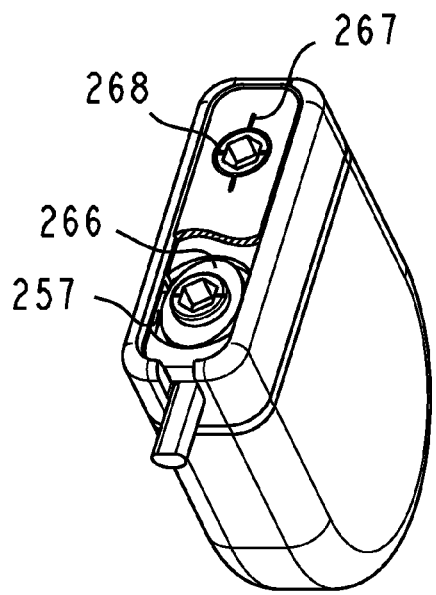
Figure 37:
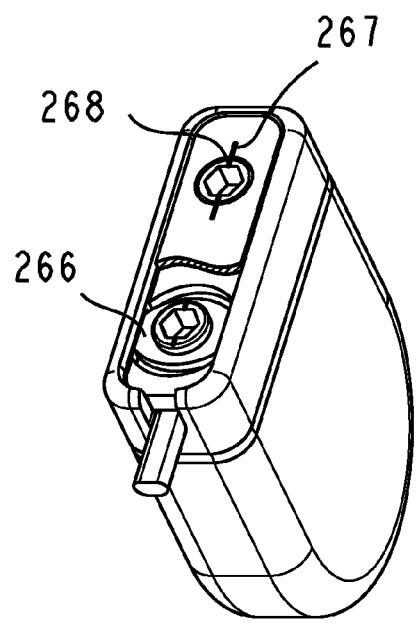
Figure 37:
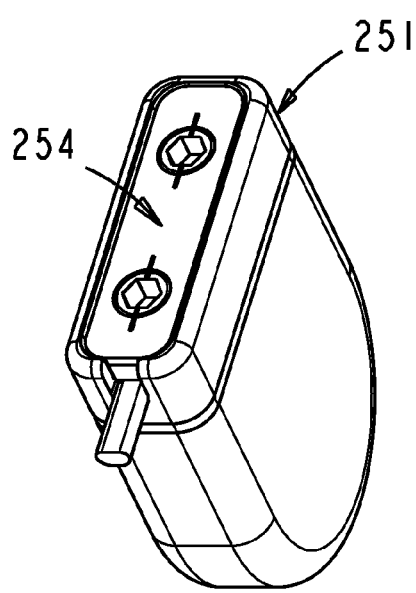

FIGS. 35-37 Connector for Flat Lead Terminal with Cam-Driven Clamping Cover

FIG. 35 is an exploded perspective view of a connector 250 comprising a feedthrough assembly 251 with integrated compressible contacts 252, a paddle-shaped lead connector terminal 253, and a clamping cover 254. The lead terminal and the clamping cover are received in a feedthrough exterior cavity 255 and their outlines match closely the outline of the feedthrough exterior cavity formed by the inside walls of the feedthrough housing 256.

The clamping cover comprises a bottom plate 257, cams 258, and a top plate 259. Each cam has a hub 261 which is rotatably held in a respective hole 262 of the top plate. The cam is captivated between the bottom plate and the top plate which are joined together, e.g., by weld joints 263. Thus constrained cam is allowed only to rotate in hole 262. Hex hole 264 enables the cam to be rotated with a hex driver.

The feedthrough housing inside walls have undercuts 265 which are used to engage the clamping cover. When the cam is rotated 90 degrees from the open or disengaged position shown in FIG. 35 the long sides 266 of the cam engage undercuts 265 as shown in the cross-sectional view of FIG. 36. Marking 267 can be used as a stationary reference for the rotating cam. When cam mark 268 is aligned with stationary mark 267, the cover is engaged and the connector and seals are pressurized.

FIGS. 37A-C show a sequence of engaging the cam-driven clamping cover to the feedthrough housing. FIG. 37A shows the lamping cover in place, but in open or disengaged position. The long sides or long axis of each cam is aligned with the feedthrough housing side walls. Cam mark 268 is at right angle to stationary mark 267.

To enable engagement of the cams the cover may be pressed manually to compress the contacts and seals or, for higher pressurization loads, the leading engagement edges of the cams can be tapered to provide the mechanical advantage as the cams are gradually engaged.

FIG. 37B shows the clamping cover in engaged condition. The long axis of the cam is at right angle to the feedthrough housing side walls and cam marks 268 are aligned with stationary marks 267. FIG. 37C shows a full view of the pressurized connector with clamping cover 254 engaged to feedthrough housing 251.

FIGS. 38A-B Connector for Iso-Diametric Leads with Cam-Driven Clamping Cover FIG. 38A is an exploded perspective view of a connector 270 comprising a feedthrough assembly 271 with integrated compressible contacts 272, a lead-seal assembly 273, and a clamping cover 274.

The clamping cover comprises a bottom plate 277, cams 278, and a top plate 279. The construction and operation of the clamping cover is similar to the one described in the preceding section. However, the bottom plate is adapted to cooperate with the lead seal assembly and to provide a smooth connector outer profile after the cover is engaged. FIG. 38B shows connector 270 in a pressurized state.

FIGS. 39-40 Modular Connectors for Flat Lead Terminals

FIG. 39A is an exploded perspective view of a connector 280 comprising a feedthrough assembly 281 with integrated compressible contacts 245, discrete seals 282, paddle-shaped lead connector terminals 283 with diagonally exiting lead 284, and cam-driven clamping covers 285. The feedthrough assembly has two substantially square exterior cavities 286 formed by the inside walls 287 of the feedthrough housing 288 and the exterior side of the dielectric substrate 289. Inside walls 287 of each exterior cavity have undercuts 290 for engaging clamping cover 285. Each feedthrough cavity further has a diagonally oriented slot 291 to provide exit for lead 284.

Each seal, lead connector terminal, and the corresponding clamping cover are received in a respective feedthrough exterior cavity 286 and their outlines match closely the outline of the feedthrough exterior cavity. The elastomeric seals may be pre-installed in the respective feedthrough cavities and retained therein by a slight interference fit. This minimizes handling of small parts and provides additional protection for the compressible contacts.

The clamping cover comprises a bottom plate 295, a cam 296, and a top plate 297. Each cam has a hub 298 and four arms 299 extending radially from the hub. The tips of the cam arms may have tapers 300 on leading engagement edges to facilitate engagement of the arms with feedthrough undercuts 290. The hub locates and rotates in a central hole 301 of the top plate. The cam is captivated between the bottom plate and the top plate which are joined together, e.g., by weld joints 302 at top outside edges of posts 303. Hex hole 304 enables the cam to be rotated with a hex driver. The cover is clamped by rotating the cam approximately 45 degrees in the clockwise direction until the cam arms stop against posts 303. Clockwise rotation of the cam to clamp the cover is consistent with tightening a screw and therefore intuitive.

The top plate has utility holes 305 which can be used to visually verify cam position. When the cam is in an open or disengaged position as seen in FIG. 39A the can arms are visible in holes 305. When the cam arms are not seen in holes 305, the cam is in a locked or engaged position and the connector is pressurized.

FIG. 39B shows a fully assembled connector. The cross-sectional view of the pressurized connector is shown in FIG. 40. The tips of cam arms 299 engage undercuts 290 on the inside walls of the feedthrough exterior cavity. Lead contacts 50 make pressure connection to the corresponding compressible contacts 245. Discrete elastomeric seals 282 are compressed to provide inter-contact and peripheral (along feedthrough cavity walls) seals.

Since the seals are decoupled from the lead terminals, seal degradation due to the time-dependent elastomer deformation are avoided. A new seal is used when a device revision is required or when a new lead is connected to the existing device. The discrete seals also enable thin flat lead connector terminals. Lead contacts 50 can be formed on a flexible or a rigid substrate or can be embedded in a hard or high durometer polymer since integral seals are not required.

FIGS. 41-42 Additional Modular Connector Configurations

The modular approach can be easily adapted to other lead counts and contact arrays. FIGS. 41A-B and 42 show devices with a single lead and four leads respectively. Similarly, the individual connectors can have contact arrays other than 2×2, e.g., 3×3, 4×4, or larger, as well as polar arrays. The connectors can also be used to connect other devices and batteries.

FIG. 41A shows a small device 310 with a single connector using the components described in the preceding section. The device further comprises a protective plug 311 which secures the clamping cover in engaged condition end prevents ingression of tissue into the hex hole.

The plug has an inner side 312 which conforms to the top of the clamping cover and an outer side 313 which provides a desirable outside profile. The inner side has a hex protrusion 314 which cooperates with hex hole 304 and two round protrusions 315 which cooperate with respective utility holes 305.

In FIG. 41B the top plate of the clamping cover has a cut away to show the clamping cover in engaged condition. Cam arms 299 are orthogonal to the feedthrough cavity inside walls and are rotated away from the diagonally disposed utility holes. After verifying that the cam arms are not visible in the utility holes, the plug protrusions can by fully inserted into the holes to prevent the cam arms to return to the open position. Only plug protrusions are shown in FIG. 41B (the plug body is cut away) to show how the pins occupy the position previously occupied by the cam arms.

FIG. 42 shows a device embodiment having a 2×2 connector array to illustrate the scalability of the modular connector system.

FIG. 43 Connector for Multiple Flat Lead Terminals with Collective Clamping Cover FIG. 43A is an exploded perspective view of a connector 320 comprising a feedthrough assembly 321 with integrated compressible contacts 245, discrete seals 282, paddle-shaped lead connector terminals 283 with diagonally exiting lead 284, and a cam-driven clamping cover 322. The connector is similar to the connector of FIG. 42, except it is adapted to engage a single cam-driven clamping cover.

The inside walls 323 of the feedthrough housing 324 have mid-side protrusions 325 and undercuts 326 for engaging clamping cover 322.

The clamping cover comprises a bottom plate 328, a cam 329, and a top plate 330. The top and bottom plates have mid-side reliefs 331 to accommodate mid-side protrusions 325 on the inside walls of the feedthrough housing. The cam is captivated between the bottom and top plates which are joined together, e.g., by weld joints 332. A hex hole 333 enables the cam to be rotated with a hex driver. The cover is clamped by rotating the cam approximately 45 degrees in the clockwise direction.

The top plate and the cam have alignment marks 334 and 335 respectively. When the cam is in a locked position, mark 335 on the cam is aligned with stationary mark 334 on the top plate of the cover. In addition, the top plate may have utility holes 336 which can also be used to visually verify cam position. When the cam is in an open or disengaged position as seen in FIG. 43A the cam body is visible in utility holes 336.

FIG. 43B show a fully assembled and pressurized connector 320. Cam marks 335 are aligned with stationary marks 334 and are pointing to utility holes 336. In addition, utility holes 336 are aligned with similar holes 337 in the cam body. After the connector is pressurized, the hex hole and the utility holes can be plugged as described earlier to prevent inadvertent rotation of the cam and to prevent tissue ingress into the holes.

FIGS. 44A-B show the connector of FIG. 43B with the top cover plate removed to show the clamping cover cam in closed and open positions respectively. A taper 338 on the leading engagement edges of the cam facilitates initial engagement with the undercuts on the feedthrough inside walls and provides mechanical advantage for the clamping action.

FIGS. 45-46 Cam-Actuated Clamping Cover with External Latches

FIG. 45 is an exploded view of a connector 340 which is a variation of connector 26 (FIG. 1) adapted for use with a cam-actuated clamping cover having external latches.

Connector 340 comprises a feedthrough assembly 341 with integrated compressible contacts 35, a paddle-shaped lead connector terminal 32, and a clamping cover assembly 342. The feedthrough housing 343 has U-shaped undercuts 344 on the feedthrough outside walls, forming detents 345 for engaging the clamping cover latches.

The clamping cover assembly comprises a base plate 350, latching members 351, cams 352, bias springs 353, and a lid 354. The lid is attached to the base plate along corresponding outside perimeter edges, preferably be a weld 355. Cam 352 has a hub 356 which is rotatably held in a hole 357 of the lid. A hex hole 358 in the cam allows the cam to be actuated by a hex driver.

Latches 359 are integrally formed on latching members 351 and protrude from the cutouts in the lid. In FIGS. 45A-B, the latches are shown in a closed condition. In order to open or spread the latches, the cams are rotated 90 degrees. The cam action spreads the latching members apart causing the latches to move outwardly.

The clamping cover can generally be installed with the latches in the closed position by simply pressing the cover against the lead terminal body until the latches snap in place over the detents. After latches 359 are engaged (FIG. 45B) they are advantageously flush with the outside walls of the feedthrough housing. In order to uninstall the clamping cover, cams 352 can be rotated 90 degrees in either direction to disengage the latches from the detents.

ADVANTAGES

From the description above, a number of advantages of various embodiments of the disclosed connector become evident:

(A) A feedthrough-based header is easier to manufacture than a molded header since it does not require fan-out wiring from feedthrough pins to contacts in the header. In contrast to the molded header, which requires sealing of the fan-out connections and forming a lead receiving cavity using molding processes, the feedthrough-based connector requires only addition of compressible contacts, to a pre-fabricated, pre-tested feedthrough.

(B) Smaller radial or transverse (x-y) contact dimensions (i.e., dimensions normal to the contact longitudinal or z-direction axis) are possible as the contact spring length is increased. Advantageously, the compressible contact can be coaxially confined in a tubular section of the feedthrough pin so that even substantial contact length does not significantly impact connector overall height.

(C) The small radial dimensions of the compressible contacts and the low effective contact height (contact tip extension into exterior feedthrough cavity) relatively independent of the contact length, enable low profile connectors with closely spaced contacts. A large number of connections can thus be provided in a small connector volume.

(D) A small connector size is achieved without compromising compressible contact performance. The high-aspect-ratio compressible contacts have a high axial (z-direction) compliance and desirable contact parameters (high deflection capability at a moderate spring rate) relative to their small radial size, which makes the contact forces less sensitive to the worst case assembly conditions and repeated mating.

(E) The compressible contacts are protected from inadvertent handling damage by being confined in a tubular body of the feedthrough pin or in a protective structure attached to the feedthrough pin. A hard contact tip can be added on top of the compressible contact to enhance contact point robustness and/or to provide contact preload for more consistent contact force.

(F) In the first embodiment of the connector for iso-diametric leads (FIG. 8), an Ω-profiled seal and a complimentarily profiled cover channel are used to safely insert the lead into the cover and to positively retain it through connector pressurization. Also advantageously, the easily achievable dimensions of this connector embodiment are a depth of approximately 5.0 mm, a length of approximately 10.5 mm, and a breadth of approximately 9.5 mm. The resulting connector volume is approximately 0.5 cc, which is less than 40% of the volume required for a comparable two-lead connector discussed in the Prior Art section above.

(G) Numerous small-sized clamping options are enabled when the metal feedthrough housing is used as the sustaining structure for connector pressurization. Small and robust engagement or retention features are possible in a metal feedthrough housing that would be impractical in a molded header. The third embodiment for iso-diametric leads demonstrates efficient use of retaining clips. The easily achievable width of this two-lead connector embodiment is 7.0 mm, which makes it suitable for a placement on an edge periphery of a small-dimensioned device. In contrast, the width of an equivalent two-lead prior art connector cited above is 13 mm. Such a drastic reduction of connector size is enabled by the use of low profile compressible contacts with small radial dimensions in combination with a space efficient retention means.

Further advantages will be evident to those skilled in the art.

RAMIFICATIONS AND SCOPE

While the connector has been described by means of specific embodiments, numerous modifications and variations known to those skilled in the art or disclosed may be employed without departing from the scope of the invention set forth in the claims. For example, the materials, dimensions, shapes, and sizes of all parts may be adapted to a particular need. The number of contacts in particular can vary greatly (up to 24 or more) thus significantly affecting envelope dimensions of a connector assembly. The feedthrough housing may be of two-piece construction, the two pieces joined by welding or another method. The exterior side of the feedthrough housing can be made of a polymer, added after feedthrough brazing operation. The lead terminal cross-sectional profile and the matching lead receiving lumen may be non-circular. The lead proximal terminal may have rectangular or oval cross-sectional profile with terminal contacts profiled accordingly. The paddle-shaped terminal may have round outline rather than paddle-shaped, with a polar rather than linear contact pad pattern. An integral seal system can be replaced with separate seal components and vice versa. Additional seal components may be added if desirable. The dielectric substrate can be a multi-layer substrate or even a two-piece construction wherein the inner piece provides a hermetic seal and the outer seal provides structural support and accommodates the compressible contacts. Additional components, such as a filter capacitor or a printed circuit board can be added to the interior side of the dielectric substrate. The compressible contacts may be installed directly into metalized holes in a dielectric substrate. As to every element, it may be replaced by one of multiple equivalent alternatives, only some of which are disclosed in the specification.

Thus the scope should be determined, not by the examples or specifics given, but by the appended claims and their legal equivalents.

I claim:

1. An implantable electrical connector assembly for separably connecting at least one implantable multi-conductor lead to an implantable device having electronic circuitry contained inside a hermetically sealed case, comprising:
   (a) a hermetic electrical feedthrough comprising a housing having inside walls which have undercuts; at least one dielectric substrate having an exterior side and an interior side, and a plurality of conductive feedthrough pins hermetically sealed in the dielectric substrate; the hermetic feedthrough having at least one exterior cavity formed by the inside walls of the feedthrough housing and the exterior side of the dielectric substrate; the feedthrough pins providing pass-through connections from the exterior cavity to the electronic circuitry in the interior of the implantable device, each feedthrough pin being adapted to accommodate a compressible contact;
   (b) at least one implantable lead comprising a proximal contact terminal having a plurality of lead contacts, each lead contact connected to at least one conductor of the multi-conductor lead, the lead contacts disposed in a pattern mapped directly to the plurality of the feedthrough pins;
   (c) a plurality of compressible contacts, each compressible contact electrically connected to a respective feedthrough pin and integrated with the feedthrough pin to form a compressible contact assembly which protectively accommodates the compressible contact, the compressible contact having an outer end adapted to making a separable electrical connection to the corresponding lead contact when the connector is pressurized;
   (d) a sealing means adapted to provide electrical isolation of each separable electrical connection when the connector is pressurized; and
   (e) a clamping cover comprising a bottom plate, a top plate, and at least one cam rotatably captivated between the top and bottom plates, the top and bottom plates joined together and generally fitting within the corresponding inside walls of the feedthrough housing, wherein after the cover is placed over at least one lead terminal in the feedthrough external cavity, the cams are aligned with the undercuts on the feedthrough housing inside walls and the cover can be engaged to and disengaged from the feedthrough housing by rotating the cams with a simple tool, whereby when the cover is engaged to the feedthrough housing, the lead contacts are forcibly mated with the compressible contacts and the sealing means is activated by being compressed against the exterior side of the dielectric substrate.

2. The connector assembly of claim 1 wherein each cam has a centrally disposed hub and a plurality of arms extending radially from the hub, each arm having an engagement tip with a tapered leading edge to facilitate the initial engagement of the tip with the undercuts on the feedthrough housing inside walls, and wherein the hub has a hex hole for rotating the cam with a hex driver.

3. The connector assembly of claim 1 wherein the top plate of the cover and the cams have alignment marks to indicate whether the cover is engaged or disengaged.

4. The connector assembly of claim 1 wherein the clamping cover has posts between the bottom and top plates, the posts adapted to limit cam rotation to a useful range and to provide a tactile feedback to indicate that the cam is rotated to a fully engaged or fully disengaged position.

5. The connector assembly of claim 1 wherein the top plate of the clamping cover has at least one utility hole to provide a visual indication whether the clamping cover is fully engaged and to allow insertion of a plug into the utility hole to securely maintain the cover in engaged condition.

6. The connector assembly of claim 1, wherein the compressible contact is a coil spring having a centrally extending filar on the outer end and the compressible contact assembly further includes a hat having a top and a bottom, wherein the top of the hat has a hole which guides the filar, and the bottom of the hat is attached to the feedthrough pin, and wherein the hat is adapted to protectively confine, retain, and preload the compressible contact.

7. The connector assembly of claim 1 wherein the compressible contact is selected from the group consisting of coil springs, fuzz buttons, and metal-particle-filled elastomer buttons.

8. The connector assembly of claim 1 wherein the feedthrough pin has a tubular section having an outer end open to the feedthrough exterior cavity, at least a portion of the tubular section and the corresponding portion of the compressible contact contained between the exterior and interior sides of the dielectric substrate.

9. The connector assembly of claim 8 wherein the compressible contact assembly further comprises a rigid contact tip and the outer end of the tubular section of the feedthrough pin is crimped to retain and to preload the compressible contact.

10. The connector assembly of claim 8, wherein the contact assembly further comprises a rigid contact tip and a washer-shaped insert, wherein the washer-shaped insert is permanently attached to the outer end of the feedthrough pin to retain and to preload the compressible contact.

11. The connector assembly of claim 1 wherein the lead contact terminal has a paddle-shaped body with a substantially flat bottom side, the paddle-shaped body containing the lead contacts, each lead contact exposed from the bottom side of the lead terminal body so that it can be accessed by the corresponding compressible contact integrated with the feedthrough pin.

12. The connector assembly of claim 11 wherein the sealing means is an integral part of the lead terminal body and wherein each lead contact is recessed from the bottom side of the lead terminal body so that the integral seal protrudes beyond the lead contacts, thereby allowing unimpeded compression of the integral seal when the terminal body is compressed between the clamping cover and the exterior side of the dielectric substrate.

13. The connector assembly of claim 11 wherein the sealing means is a discrete elastomeric seal interposed between the lead terminal and the exterior surface of the dielectric substrate, the discrete seal having an outline closely matching the outline of the feedthrough exterior cavity and having a plurality of apertures corresponding to the respective lead contacts, the apertures allowing the compressible contacts to connect to the lead contacts when connector is pressurized.

14. An implantable electrical connector assembly for separably connecting at least one implantable multi-conductor lead to an implantable device having electronic circuitry contained inside a hermetically sealed case, comprising:
  (a) a hermetic electrical feedthrough comprising a housing having inside walls and outside walls, at least one dielectric substrate having an exterior side and an interior side, and a plurality of conductive feedthrough pins; the hermetic feedthrough having at least one exterior cavity formed by the inside walls of the feedthrough housing and the exterior side of the dielectric substrate; the feedthrough pins providing pass-through connections from the exterior cavity to the electronic circuitry in the interior of the implantable device, each feedthrough pin having a profiled head adapted to accommodate a coil spring contact;
  (b) at least one implantable lead comprising a proximal contact terminal having a plurality of lead contacts, each lead contact connected to at least one conductor of the multi-conductor lead, the lead contacts disposed in a pattern mapped directly to the plurality of the feedthrough pins;
  (c) a plurality of coil spring contacts, each coil spring contact electrically connected to a respective feedthrough pin and protectively accommodated on the profiled head of the feedthrough pin to form a compressible contact assembly; the coil spring contact having an inner end and an outer end, the outer end having a centrally extending filar adapted to making a separable electrical connection to the corresponding lead contact when the connector is pressurized;
  (d) a sealing means adapted to provide electrical isolation of each separable electrical connection when the connector is pressurized; and
  (e) a clamping means adapted to detachably engage the feedthrough housing and to pressurize the connector by forcing the lead contacts against the coil spring contacts and compressing the sealing means against the exterior side of the dielectric substrate.

15. The connector assembly of claim 14 wherein the feedthrough inside walls have undercuts and the clamping means is a clamping cover comprising a bottom plate, a top plate, and at least one cam rotatably captivated between the top and bottom plates, the top and bottom plates joined together and generally matching the outline of the feedthrough inside walls, wherein after the cover is placed over at least one lead terminal in the feedthrough external cavity, the cams are aligned with the undercuts on the feedthrough inside walls and the cover can be engaged to and disengaged from the feedthrough housing by rotating the cams with a simple tool, whereby when the cover is engaged to the feedthrough housing, the lead contacts are forcibly mated with the coil spring contacts and the sealing means is activated by being compressed against the exterior side of the dielectric substrate.

16. The connector assembly of claim 14 wherein the feedthrough housing has latching detents on the outside walls, and the clamping means is a latching cover comprising a base plate, a lid, two latching members, at least one cam, and at least one bias spring, arranged so that the latches can be engaged to and disengaged from the feedthrough housing by rotating the cams with a simple tool; whereby when the cover is engaged to the feedthrough housing, the lead contacts are forcibly mated with the coil spring contacts and the sealing means is activated by being compressed against the exterior side of the dielectric substrate.

17. The connector assembly of claim 14, wherein the feedthrough housing has undercuts on the outside walls and the clamping means comprises a cover and two U-shaped spring clips having end latches, the latches adapted to engage the undercuts on the feedthrough housing outside walls, wherein the connector is pressurized by engaging the cover to the feedthrough housing with the spring clips.

18. The connector assembly of claim 14 wherein the feedthrough housing comprises at least one threaded hole and the clamping means comprises a cover and at least one threaded fastener, wherein the connector is pressurized by clamping the cover to the feedthrough housing with the fastener.

19. The connector assembly of claim 14 wherein the sealing means is a discrete elastomeric seal having at least one lumen for receiving the lead proximal terminal without significant interference, the seal having a substantially flat bottom side and an outline closely matching the feedthrough exterior cavity, and a top side cooperating with the clamping cover, the bottom side of the seal having apertures so that, after the lead terminal is inserted into the lumen to form a lead-seal assembly, each lead contact is exposed from the bottom side of the seal and can be accessed by the corresponding compressible contact integrated with the feedthrough pin, the seal providing an electrical isolation of the non-common contacts when compressed between the clamping cover and the exterior side of the dielectric substrate.

20. The connector assembly of claim 19 wherein the elastomeric seal has at least two lead-receiving lumens side-by-side, and the lead-seal assembly comprising the two leads is adapted to be accommodated in a single feedthrough exterior cavity.

21. The connector assembly of claim 14 wherein the profiled head of the feedthrough pin has a centrally disposed slot adapted to guide and protectively confine the centrally extending filar of the coil spring.

22. The connector assembly of claim 21 wherein the feedthrough pin further has a shoulder and an undercut, and the inner end of the coil spring is radially formed toward a central axis of the coil spring so that the contact can be retained on the feedthrough pin when the inner end of the coil spring snaps into the undercut.

23. The connector assembly of claim 14 wherein the compressible contact assembly further comprises a hat having a top and a bottom, the top having a cutout cooperating with a complementarily profiled head of the feedthrough pin, wherein the top of the hat is welded to the head of the feedthrough pin, whereby the hat protectively confines and preloads the coil spring contact.

24. The connector assembly of claim 23 wherein the inner end of the coil spring is attached and electrically connected to the bottom of the hat.

25. The connector assembly of claim 23 wherein the bottom of the hat is crimped to retain the coil spring contact in a preloaded condition.

26. An implantable electrical connector assembly for separably connecting at least one implantable multi-conductor lead to an implantable device having electronic circuitry contained inside a hermetically sealed case, comprising:

(a) a hermetic electrical feedthrough comprising a housing having inside walls, at least one dielectric substrate having an exterior side and an interior side, and a plurality of conductive feedthrough pins; the hermetic feedthrough having at least one exterior cavity formed by the feedthrough housing inside walls and the exterior side of the dielectric substrate; the feedthrough pins providing pass-through connections from the exterior cavity to the electronic circuitry in the interior of the implantable device, each feedthrough pin having a tubular section adapted to retain and electrically interface a compressible contact;

(b) at least one implantable lead comprising a proximal contact terminal having a body and a plurality of lead contacts, each lead contact connected to at least one conductor of the multi-conductor lead, the lead contacts disposed in a pattern mapped directly to the plurality of the feedthrough pins;

(c) a plurality of resilient compressible contacts, each compressible contact having an outer end and an inner end, the outer end extending into the feedthrough exterior cavity and providing a contact tip for separable electrical connection to the corresponding lead contact when the connector is pressurized, the inner end comprising a centrally extending tail adapted to be retained in the tubular section of the feedthrough pin;

(d) a sealing means adapted to provide electrical isolation of each separable electrical connection when the connector is pressurized; and (e) a connector clamping means, adapted to detachably engage the feedthrough housing, for supporting contact and seal compression loads, the clamping means arranged to exert pressure on the top side of the terminal body, thereby forcing the lead contacts against the compressible contacts and compressing the sealing means against the exterior side of the dielectric substrate.

27. The connector assembly of claim 26 wherein the compressible contact is a coil spring having a tapered outer end with tightly wound outer coils providing an integral contact tip.

28. The connector assembly of claim 26 wherein the exterior side of the dielectric substrate has a plurality of counterbores, and at least a portion of each compressible contact is protectively confined in the corresponding counterbore.

29. The connector assembly of claim 26 wherein the sealing means is a discrete elastomeric seal pre-assembled in the feedthrough exterior cavity, the seal having an outline closely matching the outline of the feedthrough external cavity and having a plurality of apertures corresponding to the respective compressible contacts, wherein at least a portion of each compressible contact is protectively confined in the corresponding aperture of the discrete seal.

30. The connector assembly of claim 26 wherein the compressible contact is a coil spring comprising a centrally extending filar at the outer end which provides a contact tip.

31. The connector assembly of claim 30 wherein each compressible contact has a hat having a top and a bottom, wherein the top of the hat has a hole which guides the filar, and the bottom of the hat is crimped so that the hat protectively confines and preloads the compressible contact.

* * * * *